(12) United States Patent
Marossero et al.

(10) Patent No.: US 8,275,451 B2
(45) Date of Patent: Sep. 25, 2012

(54) MATERNAL-FETAL MONITORING SYSTEM

(75) Inventors: Dorothee Marossero, Gainesville, FL (US); Tammy Y. Euliano, Gainesville, FL (US); Neil Russell Euliano, II, Gainesville, FL (US); Jose C. Principe, Gainesville, FL (US)

(73) Assignees: University of Florida Research Foundation, Inc., Gainsville, FL (US); Convergent Engineering, Inc., Gainsville, FL (US)

( * ) Notice: Subject to any disclaimer, the term of this patent is extended or adjusted under 35 U.S.C. 154(b) by 835 days.

(21) Appl. No.: 11/140,057

(22) Filed: May 27, 2005

(65) Prior Publication Data
US 2005/0267377 A1 Dec. 1, 2005

Related U.S. Application Data

(63) Continuation-in-part of application No. 10/857,107, filed on May 28, 2004, now Pat. No. 7,333,850.

(51) Int. Cl.
*A61N 1/00* (2006.01)
*A61B 5/04* (2006.01)
(52) U.S. Cl. ............ 600/511; 600/513; 607/18; 607/23
(58) Field of Classification Search .................... 607/18, 607/23; 600/511, 513
See application file for complete search history.

(56) References Cited

U.S. PATENT DOCUMENTS

| | | | |
|---|---|---|---|
| 3,703,168 A | 11/1972 | Frink | |
| 4,256,118 A * | 3/1981 | Nagel | 600/546 |
| 4,437,467 A | 3/1984 | Helfer et al. | |
| 4,489,726 A | 12/1984 | Epstein et al. | |
| 4,519,396 A | 5/1985 | Epstein et al. | |
| 4,781,200 A | 11/1988 | Baker | |
| 4,945,917 A | 8/1990 | Akselrod et al. | |
| 4,951,680 A | 8/1990 | Kirk et al. | |
| 4,967,761 A | 11/1990 | Nathanielsz | |
| 5,042,499 A | 8/1991 | Frank et al. | |
| 5,184,619 A | 2/1993 | Austin | |

(Continued)

FOREIGN PATENT DOCUMENTS

EP 310349 A2 * 4/1989

(Continued)

OTHER PUBLICATIONS

Arani et al. "Extracting uncontaminated neural signals using independent component analysis" University of California, San Diego, pp. 1-2.

(Continued)

*Primary Examiner* — Niketa Patel
*Assistant Examiner* — Nicole F Lavert
(74) *Attorney, Agent, or Firm* — Saliwanchik, Lloyd & Eisenschenk

(57) ABSTRACT

A maternal-fetal monitoring system for use during all stages of pregnancy, including antepartum and intrapartum stages. The maternal-fetal monitoring system of the subject invention comprises (1) a set of sensors; (2) an amplifying/filtering means; (3) a computing means; and (4) a graphical user interface. Accurate clinical data, which can be extracted and provided to the user in real-time using the system of the invention, include without limitation, maternal electrocardiogram (ECG) signals, maternal uterine activity signals (EHG), maternal heart rate, fetal ECG signals, and fetal heart rate. In a preferred embodiment, the maternal-fetal monitoring system of the invention includes an intelligence means, such as a neural network system, to analyze and interpret clinical data for use in clinical diagnosis antepartum, intrapartum and postpartum, as well as delivery strategy.

17 Claims, 23 Drawing Sheets

U.S. PATENT DOCUMENTS

| | | | |
|---|---|---|---|
| 5,209,237 A | | 5/1993 | Rosenthal |
| 5,301,680 A | | 4/1994 | Rosenberg |
| 5,372,139 A | * | 12/1994 | Holls et al. .................. 600/511 |
| 5,373,852 A | | 12/1994 | Harrison et al. |
| 5,397,344 A | | 3/1995 | Garfield et al. |
| 5,483,970 A | | 1/1996 | Rosenberg |
| 5,490,515 A | | 2/1996 | Mortara |
| 5,546,953 A | * | 8/1996 | Garfield .................. 600/546 |
| 5,623,939 A | | 4/1997 | Garfield |
| 5,666,959 A | * | 9/1997 | Deans et al. .................. 600/511 |
| 5,706,402 A | | 1/1998 | Bell |
| 5,724,984 A | | 3/1998 | Arnold et al. |
| 5,746,212 A | | 5/1998 | Rall et al. |
| 5,776,073 A | | 7/1998 | Garfield et al. |
| 5,785,664 A | | 7/1998 | Rosenberg |
| 5,830,848 A | * | 11/1998 | Harrison et al. .................. 424/85.2 |
| 5,957,855 A | * | 9/1999 | Oriol et al. .................. 600/511 |
| 6,053,872 A | * | 4/2000 | Mohler .................. 600/485 |
| 6,058,321 A | | 5/2000 | Swayze et al. |
| 6,115,624 A | | 9/2000 | Lewis et al. |
| 6,210,918 B1 | * | 4/2001 | Riemer .................. 435/25 |
| 6,350,237 B1 | * | 2/2002 | Pelletier et al. .................. 600/300 |
| 6,421,558 B1 | | 7/2002 | Huey et al. |
| 6,434,418 B1 | * | 8/2002 | Neal et al. .................. 600/511 |
| 6,544,170 B1 | | 4/2003 | Kajihara et al. |
| 6,594,515 B2 | | 7/2003 | Watson |
| 6,694,192 B2 | | 2/2004 | Policker et al. |
| 6,751,498 B1 | * | 6/2004 | Greenberg et al. .................. 600/511 |
| 6,816,744 B2 | | 11/2004 | Garfield et al. |
| 6,823,211 B2 | | 11/2004 | Simpson et al. |
| 6,879,858 B1 | | 4/2005 | Adams |
| 6,898,460 B2 | | 5/2005 | Hoctor et al. |
| 7,831,300 B2 | | 11/2010 | Kolluri et al. |
| 2002/0010494 A1 | | 1/2002 | Policker et al. |
| 2002/0193670 A1 | * | 12/2002 | Garfield et al. .................. 600/304 |
| 2002/0193701 A1 | | 12/2002 | Simpson et al. |
| 2003/0120159 A1 | * | 6/2003 | Mohler .................. 600/500 |
| 2003/0135130 A1 | | 7/2003 | Hoctor et al. |
| 2004/0243015 A1 | * | 12/2004 | Smith et al. .................. 600/511 |
| 2005/0105644 A1 | | 5/2005 | Baxter et al. |
| 2006/0189882 A1 | | 8/2006 | Thomas |
| 2007/0066908 A1 | | 3/2007 | Graupe et al. |
| 2007/0088226 A1 | | 4/2007 | Spence et al. |
| 2009/0177101 A1 | | 7/2009 | Hersh et al. |

FOREIGN PATENT DOCUMENTS

| | | |
|---|---|---|
| EP | 1 844 706 | 10/2007 |
| WO | WO 00/54650 | 9/2000 |
| WO | WO 03/003905 A2 | 1/2003 |
| WO | WO 03/028550 | 4/2003 |
| WO | WO 2004/084087 | 9/2004 |
| WO | WO 2005/039410 | 5/2005 |
| WO | WO 2005/044101 | 5/2005 |
| WO | WO 2005/052848 | 6/2005 |
| WO | WO 2009/013246 | 1/2009 |

OTHER PUBLICATIONS

Graupe et al. "Extraction of fetal ECG from maternal ECG early in pregnancy" *IJBEM*, 2005, vol. 7, No. 1, pp. 166-168.

He et al. "Application of ICA in removing artefacts from the ECG" *Dept. of Engineering Science*, University of Oxford, Oxford, UK, pp. 1-18.

Martens et al. "A robust fetal ECG detection method for abdominal recordings" *Physiological Measurement 28*, 2007, IOP Publishing Ltd., pp. 373-388.

Garfield, R. E. et al. "Comparing Uterine Electromyography Activity of Antepartum Patients Versus Term Labor Patients" *Am. J. Obstet. Gynecol.*, Jul. 2005, pp. 23-29, vol. 193, No. 1.

Garfield, R. E. et al. "Use of Uterine EMG and Cervical LIF in Monitoring Pregnant Patients" *BJOG*, Mar. 2005, pp. 103-108, vol. 112, Suppl. 1.

Garfield, R. E. et al. "Uterine Electromyography and Light-induced Fluorescence in the Management of Term and Preterm Labor" *J. Soc. Gynecol Investig.*, Sep./Oct. 2002, pp. 265-275, vol. 9, No. 5.

Khalil, M. et al. "Uterine EMG Analysis: A Dynamic Approach for Change Detection and Classification" *IEEE Trans. Biomed. Eng.*, Jun. 2000, pp. 748-756, vol. 47, No. 6.

Leman, H. et al. "Use of the Electrohysterogram Signal for Characterization of Contractions During Pregnancy" *IEEE Trans. Biomed. Eng.*, Oct. 1999, pp. 1222-12229, vol. 46, No. 10.

Marque, C. et al. "Uterine EHG Processing for Obstetrical Monitoring" *IEEE Trans. Biomed. Eng.*, pp. 1182-1186, Dec. 1986, vol. BME-33, No. 12.

Shafik, A. "Electrohysterogram: Study of the Electromechanical Activity of the Uterus in Humans" *Eur. J. Obstet. Gynecol. Reprod. Biol.*, pp. 85-89, vol. 73, No. 1.

Verdenik, I. et al. "Uterine Electrical Activity as Predictor of Preterm Birth in Women with Preterm Contractions" *Eur. J. Obstet. Gynecol. Reprod. Biol.*, Apr. 2001, pp. 149-153, vol. 95, No. 2.

Potter, M. et al. "Competing ICA Techniques in Biomedical Signal Analysis," *Electrical and Computer Engineering 2001*, Canadian Conference on May 13-16, 2001, pp. 987-982, vol. 2, Piscataway, NJ, USA.

Callaerts D., Moor B., Vandewalle J., Sansen W., "Comparison of SVD Methods to Extract the Foetal Electrocardiogram From Cutaneous Electrode Signals," *Med Biol Eng Comp*, 1990, 28:217-224.

Callaerts D., Sansen W., Vandewalle J., Vantrappen G., Janssens J., "Description of a Real-time System to Extract the Fetal Electrocardiogram," *Clin Phys Physiol Meas.*, 1989, 10 Suppl B:7-10. (Abstract Only).

Ferrara E.R., Widrow B., "Fetal Electrocardiogram Enhancement by Time-Sequenced Adaptive Filtering," *IEEE Trans Biomed Eng*, 1982, 29:458-60.

"Home Uterine Activity Monitoring for Preterm Labor," *JAMA*, 1993, 270:371-6.

Kanjilal P.P., Palit S., Saha G., "Fetal ECG Extraction From Single-Channel Maternal ECG Using Singular Value Decomposition," *IEEE Trans Biomed Eng*, 1997, 44:51-59.

Leman H., Marque C., Gondry J., "Use of the Electrohysterogram Signal for Characterization of Contractions During Pregnancy," *IEEE Trans Biomed Eng*, 1999, 46(10):1222-9.

Marossero D., Erdogmus D., Euliano N., Principe J., Hild K., "Independent Components Analysis for Fetal Electrocardiogram Extraction: A Case for the Data Efficient Mermaid Algorithm," *Proceedings of NNSP* (Sep. 2003), pp. 399-408, Toulouse, France.

Van Alste J.A., Schilder T.S., "Removal of Base-Line Wander and Power-Line Interference From the ECG by an Efficient FIR Filter With a Reduced Number of Taps," *IEEE Trans Biomed Eng*, 1985, 32(12):1052-1060.

Verdenik I., Pajntar M., Leskosek B., "Uterine Electrical Activity as Predictor of Preterm Birth in Women With Preterm Contractions," *Eur J Obstet Gynecol Reprod Biol.*, 2001, 95:149-153.

Zarzoso V., Nandi A.K., "Noninvasive Fetal Electrocardiogram Extraction: Blind Separation Versus Adaptive Noise Cancellation," *IEEE Trans Biomed Eng*, 2001, 48:12-18.

\* cited by examiner

FIG. 4F

Maternal Heart

Fetal Heart Model

MATERNAL-FETAL MONITORING SYSTEM

CROSS-REFERENCE TO A RELATED APPLICATION

This application is a continuation-in-part application of application U.S. Ser. No. 10/857,107, filed May 28, 2004, now U.S. Pat. No. 7,333,850, which is hereby incorporated by reference in its entirety, including all figures, tables, and drawings.

GOVERNMENT SUPPORT

This invention was made with government support under a grant awarded from the National Science Foundation under grant number 023960. The government has certain rights in the invention.

BACKGROUND OF INVENTION

Assessment of the fetus during pregnancy, and particularly during labor and delivery, is an essential but yet elusive goal. While most patients will deliver a healthy child with or without monitoring, more than 5 out of every 1,000 deliveries of a viable fetus near term is stillborn, with half having an undetermined cause of death. (National Vital Statistics System (NVSS), CDC, NCHS as published in "Healthy People 2010, Understanding and Improving Health: Chapter 16," co-authored by the Centers for Disease Control and Prevention and Health Resources and Services Administration, $2^{nd}$ Edition, U.S. Government Printing Office, November 2000). The risk of this unfortunate consequence is increased in a subgroup of "high risk" patients (e.g. diabetics). In addition to regular obstetric observation, after 23 weeks gestation antepartum ("in utero") fetal monitoring consists of the following (in order of complexity):
1. maternal report of fetal movement;
2. non-stress test (NST)—monitor fetal heart rate (FHR) by ultrasound, looking for baseline rate, variability and presence of accelerations above the baseline;
3. contraction stress test (CST)—response of the FHR to uterine contractions, either natural or induced; and
4. biophysical profile (BPP)—NST plus ultrasonographic evaluation of fetal movements and amniotic fluid volume.

Despite their wide acceptance, these tests offer limited predictive value, and give only a glimpse of the fetus at the time of testing. For high risk patients, once or twice weekly surveillance is often indicated, entailing both expense and inconvenience for the patient.

Intrapartum fetal surveillance is accomplished routinely with intermittent auscultation or continuous Doppler monitoring of the FHR, together with palpation or tocodynamometry (strain gauge) monitoring of contractions. When indicated, more invasive monitors are available, but require ruptured membranes/adequate cervical dilation, and entail some risk, primarily infectious. These monitors include, without limitation:
1. fetal scalp electrode—a wire electrode inserted into the fetal scalp;
2. intra-uterine pressure catheter (IUPC)—enables quantitative measurement of contractions; and
3. fetal scalp sampling—a blood sample drawn for pH analysis.

Contraction detection allows monitoring of the progress of labor. The tocodynamometer detects only the presence or absence of tension on the abdomen (whether from uterine contraction or maternal movement), and often fails in the presence of obesity. When cervical dilation lags behind the anticipated labor curve, oxytocin is often indicated to induce a more effective contraction pattern. Safe titration of the oxytocin may require accurate determination of "Montevideo units" which measure the strength of uterine contractions over 10 minutes. This requires the more invasive IUPC, a catheter placed into the uterus, alongside the fetus, to measure the pressure generated by uterine contractions.

The rationale for use of intrapartum electronic fetal monitoring (EFM) assumes that FHR abnormalities accurately reflect hypoxia (inadequate oxygen to the fetus), and that early recognition of this could induce intervention to improve outcome for both mother and fetus. Unfortunately, numerous studies have failed to identify this improved outcome with the use of EFM in low-risk deliveries. In fact some studies have actually shown an increase in morbidity from a higher operative delivery rate. Perhaps this should not be surprising in light of the variability in interpretation of FHR tracings and their lack of specificity for hypoxia. Yet, continuous EFM remains the standard of care in US hospitals, in large part due to medicolegal concerns. Meanwhile researchers seek an alternative monitor, specific for fetal well being, preferably one that is non-invasive and comfortable for the mother, with reliable, reproducible interpretation. Recently, analysis of the fetal ECG (electrocardiogram) has held promise, with some features of the waveform more specifically indicating fetal hypoxia. Use of the waveform analysis reduced the incidence of severe metabolic acidosis at birth, while necessitating fewer scalp samples and operative deliveries. Unfortunately, acquisition of the FECG was through the fetal scalp electrode described above which is both invasive and limited in its application. The necessity for access to the fetal scalp requires both adequate cervical dilation and ruptured membranes, eliminating this procedure for antepartum fetal surveillance, as well as early labor.

Non-invasive acquisition of the FECG is a recognized issue of mixed signals. Electrodes placed on the skin surface will record all transmitted electrical activity including maternal ECG, maternal skeletal muscle, uterine muscle, fetal skeletal muscle, and fetal ECG.

Uterine contractions are the result of the coordinated actions of individual myometrial cells. At the cellular level, the contractions are triggered by a voltage signal called an action potential. During pregnancy, cellular electrical connectivity increases such that the action potential propagates to produce a coordinated contraction involving the entire uterus. The action potential during a uterine contraction can be measured with electrodes placed on the maternal abdomen resulting in a uterine EMG signal (hereinafter referred to as "EHG": electrohysterogram). Specifically, the EHG signal can be processed to produce a signal that is similar to the standard uterine activity signal from the tocodynamometer or IUPC. The EHG provides contraction frequency and duration information. To date, EHG signals have not been used in assessing the intra-uterine pressure or predicting montevideo units.

Postpartum, continuous uterine contraction is required to minimize uterine bleeding from the placental detachment site. Hemorrhage is the leading cause of peripartum maternal death, and most of these are postpartum hemorrhage due to this "uterine atony." Current monitoring consists of serial uterine palpation at intervals of several hours. Diagnosis is usually made by patient complaint of severe bleeding, or hypovolemic shock (from hemorrhage). Neither IUPC nor tocodynamometer monitoring is available at this time. The EHG would provide a unique means for monitoring the uterine tone, providing an early warning of atony and potential hemorrhage.

Devices that utilize invasive techniques for monitoring fetal health include those disclosed in U.S. Pat. Nos. 6,594,515; 6,115,624; 6,058,321; 5,746,212; 5,184,619; 4,951,680; and 4,437,467.

To address the inadequacies noted above, various methods have been proposed for use in processing maternal abdominal signals to provide more accurate FECG extraction. These methods include subtractive filtering (see, for example, U.S. Pat. No. 4,945,917), adaptive filtering (see, for example, Widrow, B. et al., "Adaptive Noise Canceling: Principals and Applications," *Proc. IEEE,* 63(12):1692-1716 (December 1975); Adam, D. and D. Shavit, "Complete Fetal ECG Morphology Recording by Synchronized Adaptive Filtration," *Med. & Biol. Eng. & Comput.,* 28:287-292 (July 1990); Ferrara, E. and B. Widrow, "Fetal Electrocardiogram Enhancement by Time Sequenced Adaptive Filtering," *IEEE Trans. Biomed. Eng.,* BME-29(6):458-460 (June 1982); U.S. Pat. Nos. 4,781,200 and 5,042,499), orthogonal basis (Longini, R. et al., "Near Orthogonal Basis Function: A Real Time Fetal ECG Technique," *IEEE Trans. On Biomedical Eng.,* BME-24(1):39-43 (January 1977); U.S. Pat. No. 5,042,499), linear combination (Bergveld, P. et al., "Real Time Fetal ECG Recording," *IEEE Trans. On Beiomedical Eng.,* BME-33(5):505-509 (May 1986)), single value decomposition (Callaerts, D. et al., "Comparison of SVD Methods to Extract the Fetal Electrocardiogram from Cutaneous Electrodes Signals," *Med. & Biol. Eng. & Comput.,* 28:217-224 (May 1990); U.S. Pat. No. 5,209,237), and MECG averaging and correlation (Abboud, S. et al., "Quantification of the Fetal Electrocardiogram Using Averaging Technique," *Comput. Biol. Med.,* 20:147-155 (February 1990); Cerutti, S. et al., "Variability Analysis of Fetal Heart Rate Signals as Obtained from Abdominal Electrocardiographic Recordings," *J. Perinat. Med.,* 14:445-452 (1986); J. Nagel, "Progresses in Fetal Monitoring by Improved Data Acquisition," *IEEE Eng. Med. & Biol. Mag.,* 9-13 (September 1984); Oostendorp, T. et al., "The Potential Distribution Generated by Fetal Heart at the Maternal Abdomen," *J. Perinat. Med.,* 14:435-444 (1986); U.S. Pat. No. 5,490,515). These methods, unfortunately, do not reliably enable continuous extraction of maternal-fetal data or cannot capture a comprehensive account of maternal-fetal health based on a combination of test results (i.e., fetal heart rate, fetal ECG, maternal ECG, and maternal uterine activity (EHG)).

Recently, magnetocardiography has been utilized in extracting fetal ECG (see, for example, Sturm, R. et al., "Multi-channel magnetocardiography for detecting beat morphology variations in fetal arrhythmias," *Prenat Diagn,* 24(1):1-9 (January 2004); and Stinstra, J. et al, "Multicentre study of fetal cardiac time intervals using magnetocardiography," *BJOG,* 109(11):1235-43 (November 2002)). Unfortunately, magnetocardiography is limited in application, technologically complex, and difficult to administer to assess accurate fetal ECG readings.

Accordingly, a cost-effective, portable monitoring system for both the mother and fetus is needed that can continuously monitor, in real-time, and accurately extract and evaluate maternal/fetal heart rates and ECGs, maternal EHG, as well as fetal position.

BRIEF SUMMARY OF THE INVENTION

The present invention provides an effective, all-inclusive system for maternal-fetal monitoring during both antepartum and intrapartum stages of pregnancy. In one embodiment, the system uses a set of electrodes on the maternal abdomen to extract clinical data. Clinically relevant data that can be extracted from these electrodes include, without limitation, maternal electrocardiogram (ECG), maternal uterine EMG (EHG), fetal heart rate (FHR), fetal ECG, and determination of fetal position. The maternal-fetal monitoring system of the present invention can be used for antepartum and/or intrapartum monitoring.

In a preferred embodiment, the system also incorporates an intelligence means, such as a neural network system, that utilizes the clinical data to analyze and interpret fetal well-being (both antepartum and intrapartum). The intelligence means can also offer clinical advice including, but not limited to, fetal distress, maternal distress, labor progress, contraction effectiveness, uterine rupture, likelihood of delivery within a defined period (i.e., preterm evaluation), and likelihood of successful vaginal delivery. Furthermore, immediate postpartum monitoring of the EHG can provide the user with information regarding uterine tone (i.e., pre-delivery and/or post-delivery). For example, the subject monitoring system can signal uterine atony and prompt early intervention.

The present invention provides comprehensive monitoring/classification of maternal-fetal health through the use of novel methods for accurately extracting maternal ECG, heart rate and uterine activity (EHG), as well as fetal ECG, heart rate, and positioning, including (1) using an independent component analysis algorithm (ICA) to separate maternal and fetal signals; (2) using signal processing means for automatically determining the fetal and maternal channels, (3) using signal processing means for providing contraction information (4) using signal processing means for providing undistorted ECG waveforms (P and T waves and QRS complex) post-ICA source separation; (5) using a surface electrode mesh to provide accurate positioning and repeatability in extracting fetal ECG signals, higher signal quality and higher separation performance, and enhance patient comfort; and (6) using a neural network to present clinical observations regarding maternal and fetal health (i.e., fetal distress, maternal distress, labor progress, contraction effectiveness, likelihood of delivery within a defined period) in view of clinical services to be provided.

The algorithms utilized in the present invention are particularly advantageous in that they enable the maternal-fetal monitoring system to provide real-time results as well as automatic and real-time classification of maternal and fetal channels of output using portable, low power digital signal processor implementations.

The subject invention also provides an EHG monitor. In one embodiment, the monitoring system includes at least one sensor to acquire a uterine EMG signal and a signal processor for generating a signal representative of uterine activity (EHG). The EHG indicates uterine contraction frequency and contraction duration information. Additionally, the EHG approximates a signal that would be acquired using either a toco or, after processing, approximates a signal that would be acquired using an intra-uterine pressure catheter (IUPC) sensor. In a preferred embodiment, the electrodes of the system would simultaneously collect both ECG and EHG information.

The maternal-fetal monitoring system of the present invention is particularly advantageous as either an add-on or stand-alone monitor for use in a variety of settings. As an all-inclusive monitoring system, the maternal-fetal monitoring system of the present invention can be effectively used in place of non-stress tests, contraction stress tests, biophysical profiles, preterm labor evaluations, and existing fetal monitoring systems. Moreover, by providing an all-inclusive monitoring system, which includes an intelligence means for offering clinical advice, the present invention can provide improved prediction of maternal/fetal well-being as well as prediction of labor progress as compared to existing fetal monitoring systems. The system also provides the ability to monitor maternal and/or fetal well-being during surgery (both cesarean section and non-obstetric surgery in the pregnant patient) without interfering with the sterile field. In addition, the system provides the only means to continuously monitor postpartum uterine tone.

Certain embodiments can be portable for use in a clinical office/hospital setting as well as at home. Because the maternal-fetal monitoring system of the present invention can be used in a home setting, trips to the hospital or clinical office can be limited. For example, the monitoring system of the invention can limit trips to the hospital to investigate contractions (i.e., Braxton Hicks contractions) versus labor for both pre-term and at term mothers that must travel a fair distance to the hospital.

The maternal-fetal monitoring system of the present invention enables non-invasive capture of fetal ECG results with much less risk to the fetus' health and no limitation on cervical dilation or ruptured membranes, as is generally presented with use of current systems and methods for monitoring fetal ECG. The system eliminates uncomfortable equipment, and can be used intraoperatively during Cesarean delivery as well as during non-obstetric surgery in the pregnant patient (i.e., appendectomy or cholecystectomy where ultrasound would be in the sterile field).

BRIEF DESCRIPTION OF DRAWINGS

FIGS. 4A-F are examples of computer user-interface pages presented to a user in accordance with the subject invention.

DETAILED DISCLOSURE

Figure 1:
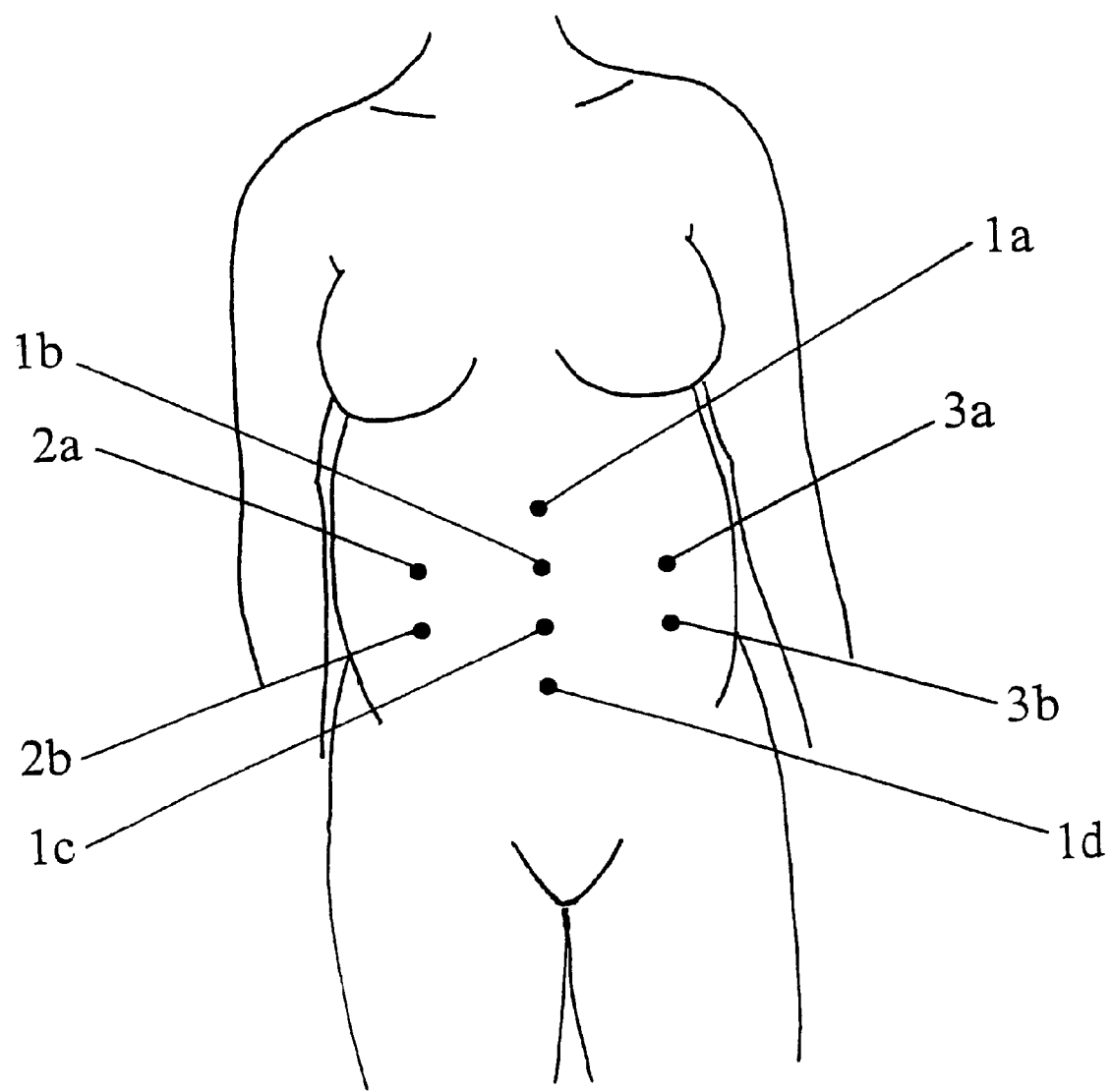
FIG. 1 illustrates a set of electrodes positioned on a maternal abdomen in accordance with the subject invention.

The subject invention provides a system for non-invasive, comprehensive monitoring of maternal-fetal vital signs for use in interpreting maternal-fetal health as well as in offering support/advice in making clinical decisions. The system comprises (1) at least one surface sensor for extraction of maternal and fetal vital signs, including contractions; (2) a data storage device for collecting sensor input (i.e., maternal and fetal vital signs); (3) a computing means for receiving and analyzing sensor input (vital signs) to accurately determine clinical data, including without limitation, maternal and fetal vital signs, fetal presentation, contraction efficiency, and pharmaceutical efficacy (i.e., titration of oxytocin). A graphical user interface can be included with the systems of the invention to display clinical data as well as enable user-interaction.

In one embodiment, the system of the invention further includes an intelligence system that can use the clinical data generated by the processor in offering support/advice for making clinical decisions (i.e., to interpret fetal well-being, labor progress, likelihood of delivery within a period of time; and likelihood of successful vaginal delivery). An intelligence system of the subject invention can include, but is not limited to, artificial neural networks, fuzzy logic, evolutionary computation, knowledge-based systems, optimal linear or nonlinear filtering, and artificial intelligence.

In one embodiment, a neural network system is provided in the monitoring system of the invention to enable real-time assistance in providing additional clinical data (i.e., classification of fetal health and detection of abnormalities, for example arrhythmias, bradycardia, tachycardia, or problems with umbilical cord or with fetal presentation).

In accordance with the subject invention, the computing means is preferably a digital signal processor, which can (1) automatically, accurately, and in real-time, extract maternal and fetal vital signals, including ECG signals, and EHG signals from sensor input; (2) assess the quality of clinical data (i.e., maternal and fetal vital signals) provided by the processor in view of environmental noise; (3) determine fetal presentation; (4) determine contraction efficiency; (5) determine probability of vaginal delivery; (6) determine time to delivery; (7) determine arrested descent; (8) determine uterine rupture, and (9) determine labor progress.

In one embodiment, the system of the subject invention is stationary. For example, the system of the invention can be used within a healthcare setting (i.e., hospital, physician's office).

In another embodiment, the system of the subject invention is portable for use outside of a healthcare setting (i.e., home use). In a related embodiment, a portable system enables continuous monitoring of the mother and fetus for beneficial assessment of maternal-fetal wellbeing (i.e., in general, specific activities/environments—exercising and/or presence of effective contraction to determine labor). Such monitoring can provide information not only to the user (i.e., mother) but also provide off-site information to the healthcare provider. For example, continuous monitoring can be accomplished remotely from the location of mother/fetus by the healthcare provider.

Definitions

As used herein, the term "vital signs" or "vital signals" includes maternal and fetal heart rate, respiratory rate, ECG results, and EHG.

As used herein, the term "clinical data" refers to information obtained from the analysis and/or interpretation of maternal-fetal vital signs. Clinical data can include, but is not limited to, classification of maternal and fetal health (i.e., normal fetal heart rate or normal maternal heart rate during labor), fetal presentation, labor progress, contraction efficiency, pharmaceutical efficacy/toxicity, arrhythmias, bradycardia, tachycardia, problems with umbilical cord or with fetal presentation, and postpartum uterine atony.

The term "patient," as used herein refers to a mother and/or fetus. The term patient includes mammals to which monitoring systems according to the present invention are provided. Mammalian species that benefit from the disclosed monitoring systems include, but are not limited to, humans, domesticated animals (i.e., dogs, cats, horses), as well as rare animals that require observation (i.e., endangered mammals).

Sensors

In accordance with the subject invention, vital signs (and corresponding clinical data) are extracted in real time using sensors that do not endanger fetal health. In a preferred embodiment, a set of electrodes is used to sense maternal-fetal vital signs.

One embodiment of the invention utilizes a set of electrodes (at least 4 electrodes but preferably 10 up to 20 electrodes) provided on a mesh (or vest), wherein the mesh can function as an electrode-stabilization component. Such a mesh can be prepared using any suitable material that permits the mesh to be both lightweight and comfortable. The benefits of a system of this type are the ease of use and reduction of preparation time required to appropriately place the electrodes on a patient. For example, preparation time can be reduced from 15-30 minutes for adhesive-based disposable electrodes to about 5 minutes using a mesh of the invention. In addition, a mesh of electrodes according to the subject invention would permit consistent (and repeatable) extraction of maternal-fetal vital signs.

As illustrated in FIG. 1, a set of eight electrodes are positioned such that four electrodes, 1*a-d*, are placed on the vertical mid-line of the abdomen, above and below the maternal navel. The remaining four electrodes are positioned so that two electrodes are to the left, 2*a-b*, and to electrodes are to the right, 3*a-b*, of the mid-line vertically aligned four electrodes. In a preferred embodiment, the left leg and driven right leg reference electrodes would be placed in the center of the abdomen between electrodes 2*a* and 2*b*.

Amplifier

An amplifier is provided in the monitoring system of the invention to amplify maternal-fetal vital signals collected by the set of sensors of the invention. Amplifiers for use in the collection of vital signals are known in the art. For example, traditional ECG amplifiers amplify an input signal from an electrode sensor in the range of 1 mV to 5 mV in amplitude. Unfortunately, such amplifiers are not always suitable for fetal ECG because the fetal ECG signal is typically in the range of about 10 µV to 50 µV in amplitude. Thus, the fetal ECG is often hidden below the noise floor. To address this, the amplifier of the subject invention is calibrated such that the fetal vital signals are sufficiently amplified for detection while preserving the dynamic range of the maternal vital signals.

In one embodiment, the amplifier of the invention is a high-resolution, low-noise, unipolar amplifier (i.e., all channels of signals are referenced from a single electrode). In a preferred embodiment, a driven right leg (DRL) circuit is utilized to actively suppress noise and improve the common mode rejection ratio (CMRR) of the amplifier so that the fetal ECG is above the noise floor. More preferably, the amplifier amplifies input signals by 1,500 times, has eight channels, can be adjusted between 4,000 V/V and 10,000 V/V, and has a CMRR of at least 80 dB.

Figure 2:
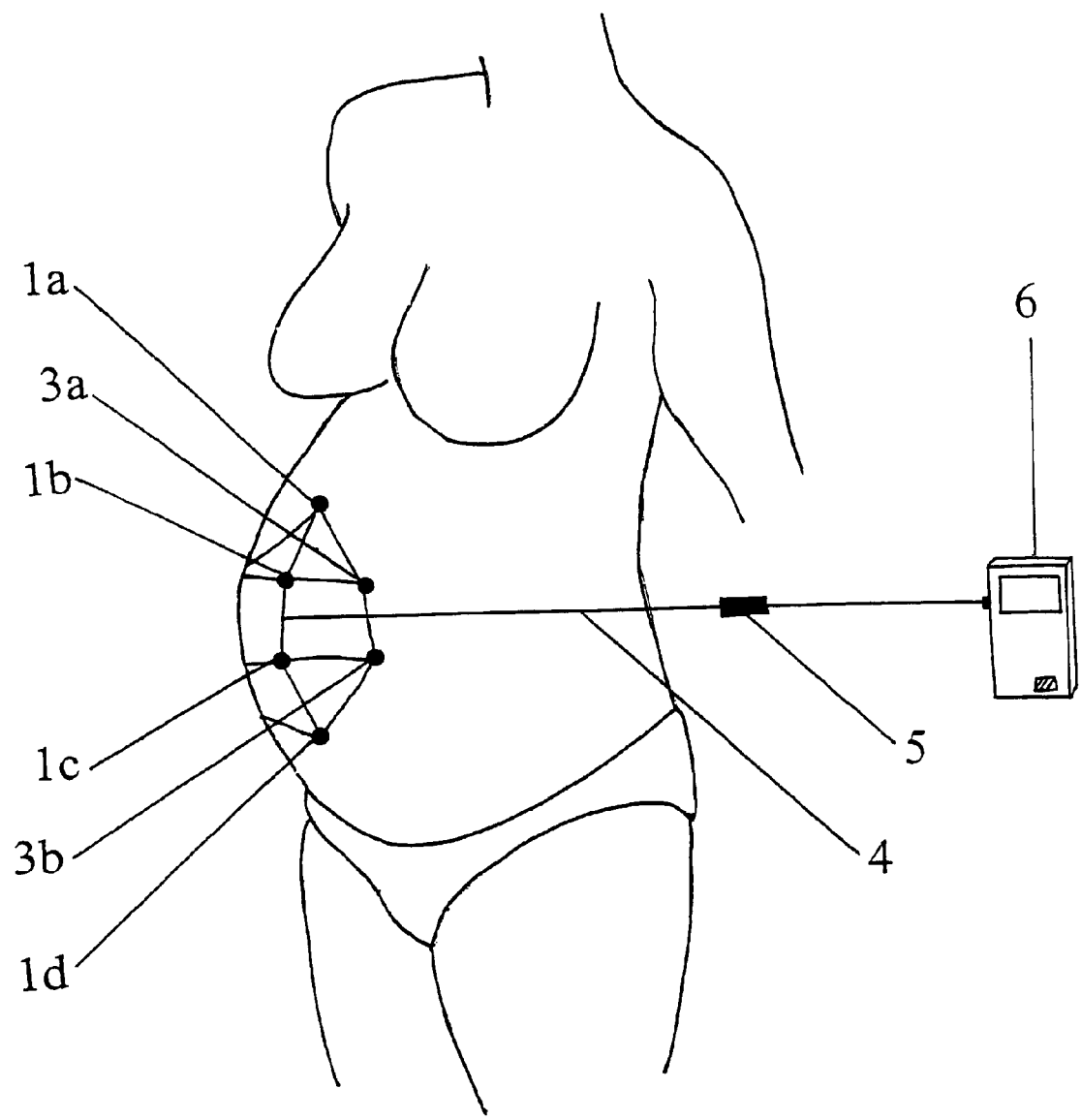
FIG. 2 illustrates one embodiment of the maternal-fetal monitoring system, wherein the monitoring system is ambulatory.

In another embodiment, as illustrated in FIG. 2, the amplifier 5 has a 15-pin D-sub connector that interfaces with an electrode cable 4 connected to a set of electrodes 1*a-d*, 3*a-b*. Preferably, the electrode cable is a 10-lead shielded ECG cable. A shielded cable is essential to reduce any noise interference due to frequencies from various power sources. But other means of providing shielding such as fiber optical cables are preferred. In one embodiment, amplifier output can interface to an analog-to-digital converter (A/D) converter. A power supply is provided to operate the amplifier. Preferably, the power supply includes an adapter that is a 12V AC-DC medical grade power supply adapter and a power converter, which is provided to protect the patient from leakage currents.

The A/D converter can be situated in the amplifier or in a computing means 6 of the invention. An A/D converter can be selected from a variety of suitable types known in the art that have the desired dynamic input range. A/D converters encode sensor signals for respective sensor channels into a digital format, such as a 16 bit format, at a desired sampling rate, such as 200 Hz.

Filters

According to the subject invention, at least one filter can be included in the maternal-fetal monitoring system. Filters of the invention can be applied to sensor signals prior to processing, during processing, or post processing as performed in the computing means; or some combination thereof. In certain embodiments, the filter(s) are applied at the amplifier to signals communicated from the sensors, prior to any processing performed by the computing means. In a related embodiment, filters are also applied to signals during and after processing by the computing means (i.e., filters applied prior to and during ICA algorithm operations, and/or applied to ICA operations output). In certain embodiments, linear or non-linear filtering is performed by an intelligence system of the subject invention.

Filters of the invention can be analog filters, such as those used for suppressing specific frequency components, which are well known in the art. Further, digital filters are also contemplated for use in the subject monitoring system. In certain embodiments, digital filtering operations are accomplished using a computing means, preferably a computer processor (i.e., microprocessor or digital signal processor (DSP)).

By using filter(s), important signal components can be easily examined by filtering out undesired spectral components such as noise. According to the subject invention, filtering operations that can be used, either alone or in combination, in extracting vital signal components include, but are not limited to, finite impulse response (FIR) filters and infinite impulse response (IIR) filters, such as band-pass filters, high pass filters, low pass filters, band-stop (or "notch") filters, and also to non-linear filters such as the median filter.

In certain embodiments, at least one band pass filter and/or low pass filter is applied to vital signals prior to processing with ICA algorithm operations. In related embodiments, band pass filters are applied to EMG/EHG signals or to ECG signals. In another embodiment, the FIR filter(s) is applied to ECG signals. In yet another embodiment, inverse filter(s), with or without band pass filter(s), are applied to post-processed vital signals to further refine clinical data provided by the vital signals (i.e., maternal and fetal ECG).

In a preferred embodiment, the low pass filter is a butterworth filter. When a band pass filter is applied, the cut-off frequency is 100 Hz. Most preferably, a combination of band pass filter(s) and notch filter(s) is applied to vital signals, wherein the pass band is 0.16 Hz and 100 Hz, and the specific frequency of the notch filter is 60 Hz.

Hardware

Maternal-fetal vital signals (i.e., ECG, and EHG signals) obtained in accordance with the subject invention are transmitted from the sensors to a computing means for signal processing. The computing means can also be responsible for maintenance of acquired data as well as the maintenance of the maternal-fetal monitoring system itself. The computing means can also detect and act upon user input via user interface means known to the skilled artisan (i.e., keyboard, interactive graphical monitors).

In one embodiment, the computing means further comprises means for storing and means for outputting processed data. The computing means includes any digital instrumentation capable of processing signals from the sensors of the invention (i.e., ECG signals). Such digital instrumentation, as understood by the skilled artisan, can process communicated signals by applying algorithm and filter operations of the subject invention. Preferably, the digital instrumentation is a microprocessor, a personal desktop computer, a laptop, and/or a portable palm device. The computing means can be general purpose or application specific.

The subject invention can be practiced in a variety of situations. The computing means can directly or remotely connect to a central office or health care center. In one embodiment, the subject invention is practiced directly in an office or hospital. In another embodiment, the subject invention is practiced in a remote setting, for example, personal residences, mobile clinics, vessels at sea, rural villages and towns without direct access to healthcare, and ambulances, wherein the patient is located some distance from the physician.

In a related embodiment, the computing means is a custom, portable design and can be carried or attached to the patient in a manner similar to other portable electronic devices such as a portable radio, or interwoven in the patient clothing as a wearable computer.

Figure 3:
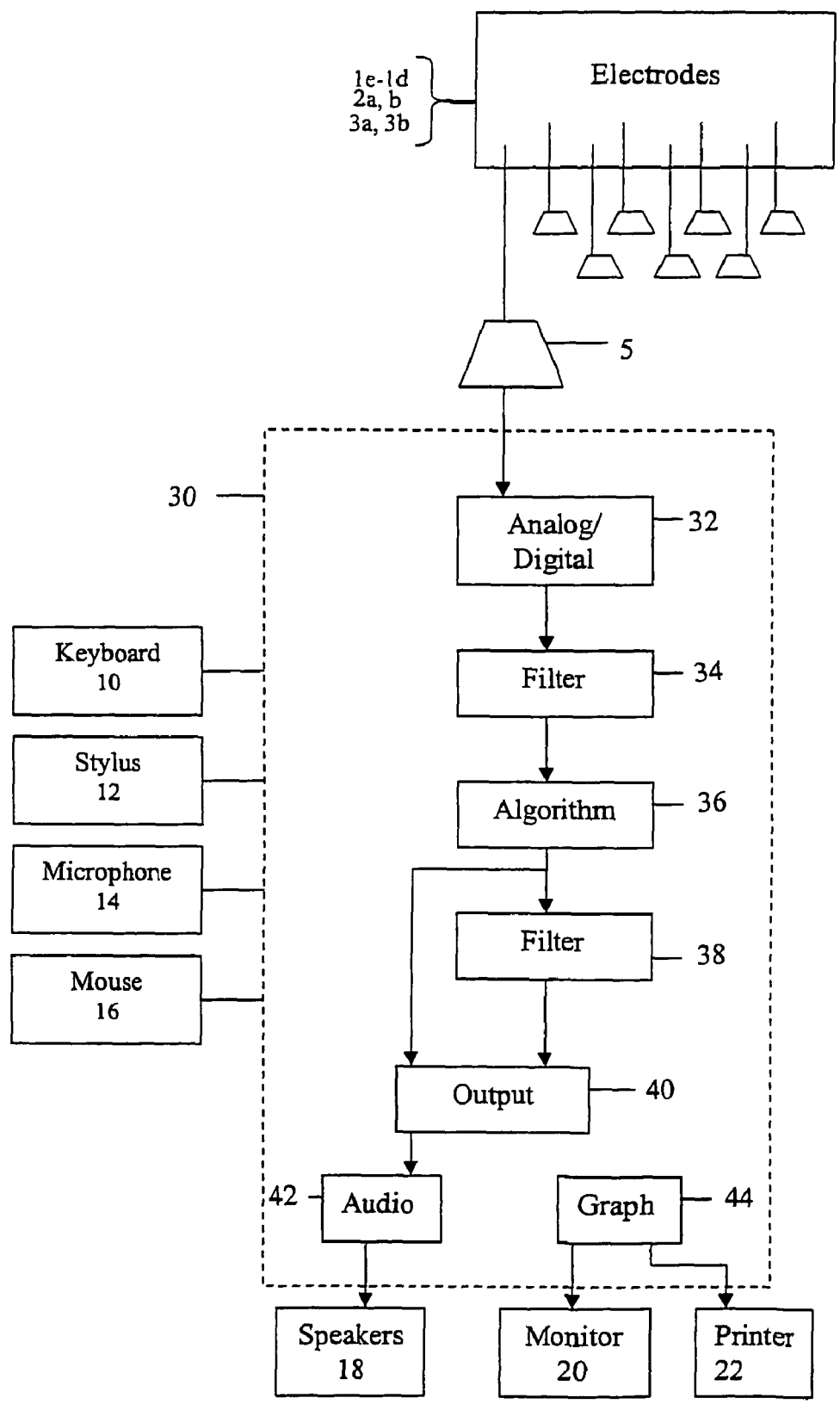
FIG. 3 illustrates a computing means used in accordance with the subject invention.

Referring to FIG. 3, the computing means used in accordance with the subject invention can contain at least one user-interface device including, but not limited to, a keyboard 10, stylus 12, microphone 14, mouse 16, speaker 18, monitor 20, and printer 22. Additional user-interface devices contemplated herein include touch screens, strip recorders, joysticks, and rollerballs.

Preferably, the computing means comprises a central processing unit (CPU) 30 having sufficient processing power to perform algorithm operations in accordance with the subject invention. The algorithm operations 36, including the filtering operations 34 and 38, can be embodied in the form of computer processor usable media, such as floppy diskettes, CD-ROMS, zip drives, non-volatile memory, or any other computer-readable storage medium, wherein the computer program code is loaded into and executed by the computing means. Optionally, the operational algorithms of the subject invention can be programmed directly onto the CPU using any appropriate programming language, preferably using the C programming language.

In certain embodiments, the computing means comprises a memory capacity sufficiently large to perform algorithm operations in accordance with the subject invention. The memory capacity of the invention can support loading a computer program code via a computer-readable storage media, wherein the program contains the source code to perform the operational algorithms 36 of the subject invention. Optionally, the memory capacity can support directly programming the CPU to perform the operational algorithms of the subject invention. A standard bus configuration can transmit data between the CPU, memory, ports and any communication devices.

In addition, as understood by the skilled artisan, the memory capacity of the computing means can be expanded with additional hardware and with saving data directly onto external mediums including, for example, without limitation, floppy diskettes, zip drives, non-volatile memory and CD-ROMs.

As described above, the computing means can include an A/D converter to translate analog signals into digital signals 32 (i.e., an analog/digital card). The A/D converter preferably readies the signals for further processing according to the subject invention. Additional filtering steps may precede any algorithmic operations of the invention.

The computing means can further include the necessary hardware and software to convert processed signals into an output form 40 readily accessible by the trained physician, nurse practitioner, midwife, or technician. For example, without limitation, an audio device 42 in conjunction with audio speakers 18 can convert and play a processed fetal heartbeat into an audio signal, and/or a graphical interface 44 can display ECG signals in a graphical form on a monitor 20 and/or printer 22. Further, the computing means can also include the necessary software and hardware to receive, route and transfer data to a remote location.

In one embodiment, the patient is hospitalized, and clinical data generated by a computing means is transmitted to a central location, for example, a monitoring station located in a maternity ward, or to a specialized physician located in a different locale.

In another embodiment, the patient is in remote communication with the health care provider. For example, patients can be located at personal residences, mobile clinics, vessels at sea, rural villages and towns without direct access to healthcare, and ambulances, and by using the maternal-fetal monitoring system of the invention, still provide clinical data to the health care provider. Advantageously, mobile stations, such as ambulances, and mobile clinics, can monitor maternal-fetal health by using a portable computing means of the subject invention when transporting and/or treating a patient.

To ensure patient privacy, security measures, such as encryption software and firewalls, can be employed. Optionally, clinical data can be transmitted as unprocessed or "raw" signal(s) and/or as processed signal(s). Advantageously, transmitting raw signals allows any software upgrades to occur at the remote location where a computing means is located. In addition, both historical clinical data and real-time clinical data can be transmitted.

Communication devices such as wireless interfaces, cable modems, satellite links, microwave relays, and traditional telephonic modems can transfer clinical data from a computing means to a healthcare provider via a network. Networks available for transmission of clinical data include, but are not limited to, local area networks, intranets and the open internet. A browser interface, for example, NETSCAPE NAVIGATOR or INTERNET EXPLORER, can be incorporated into communications software to view the transmitted data.

Figure 4A:
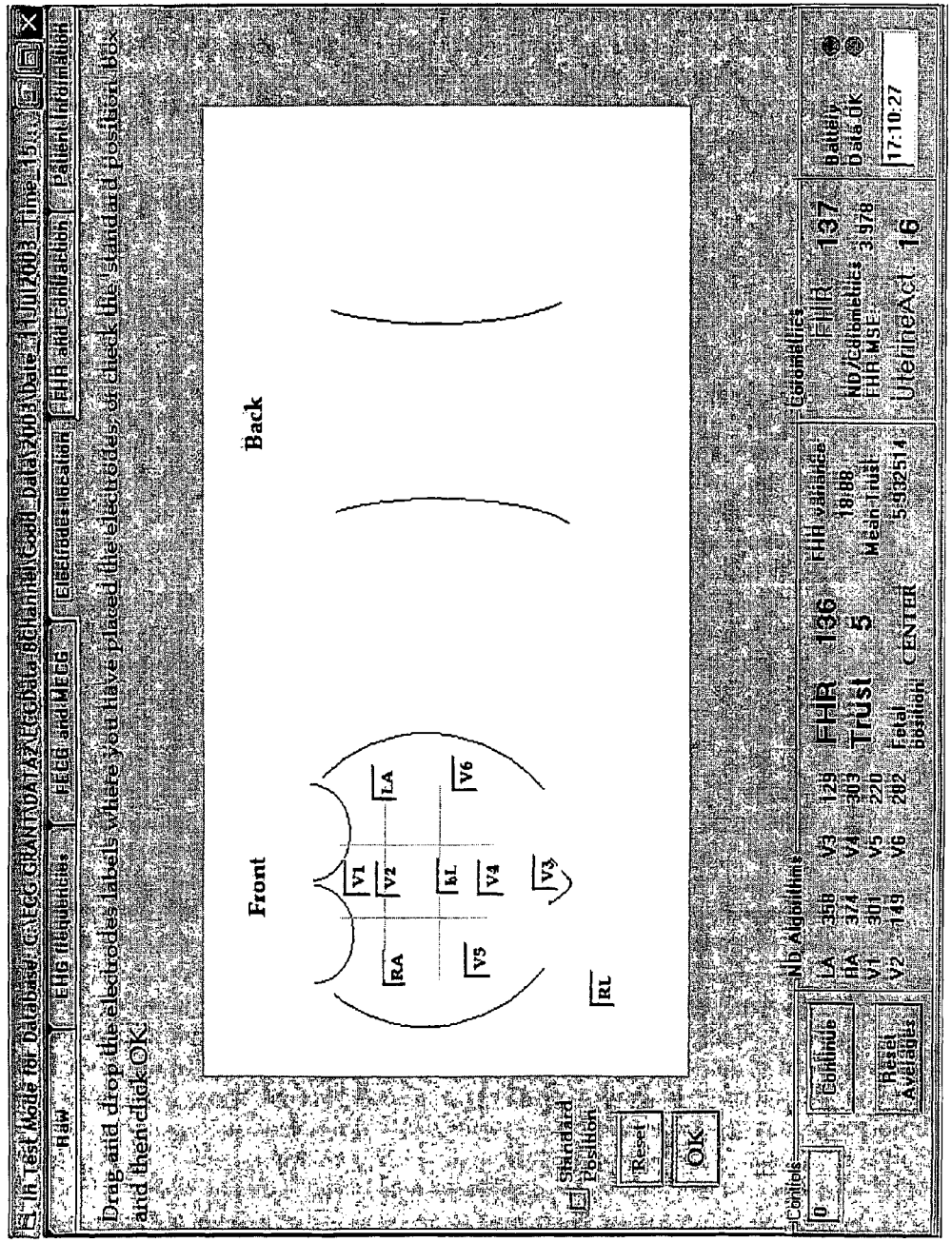
Figure 4B:
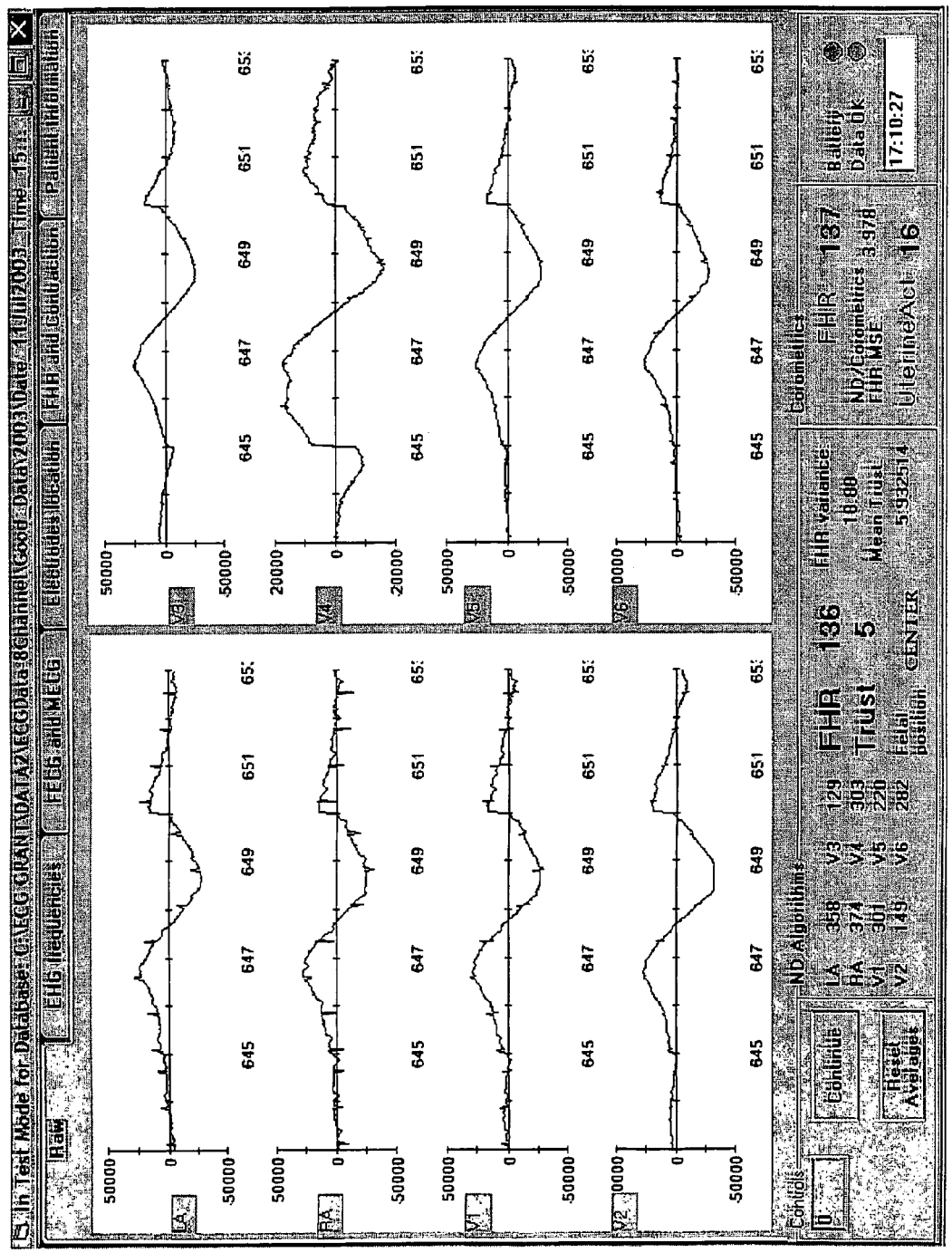
Figure 4C:
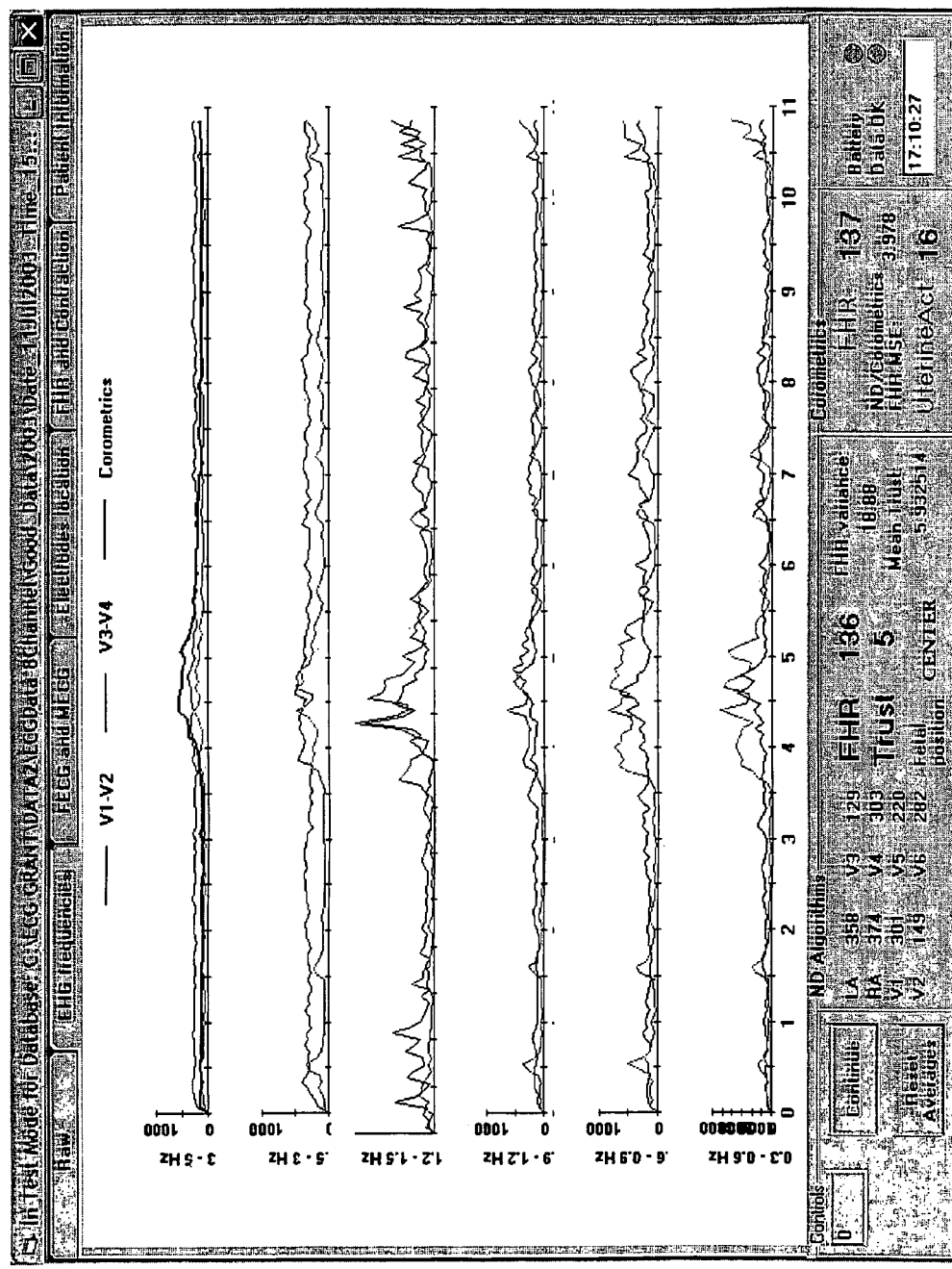
Figure 4D:
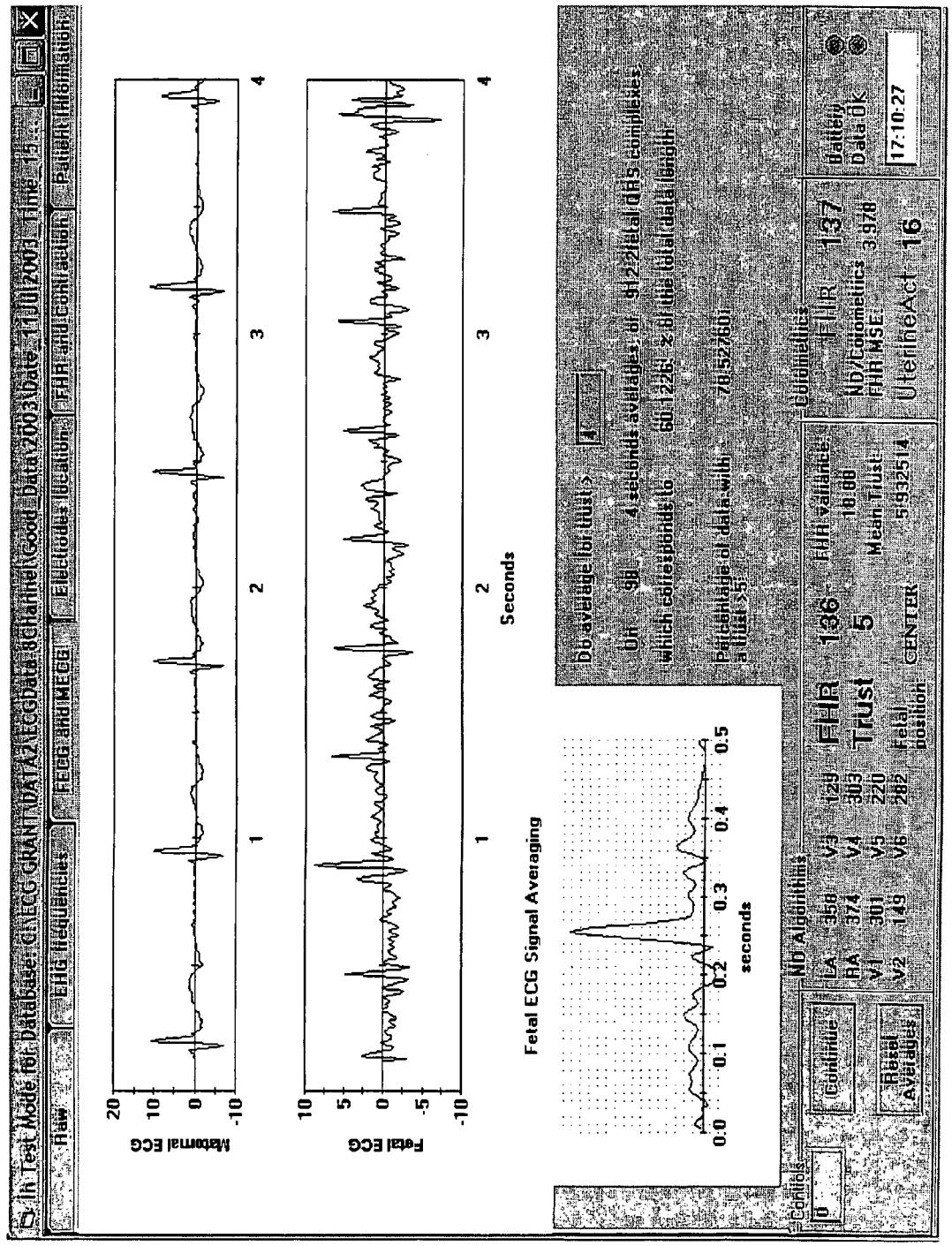
Figure 4E:
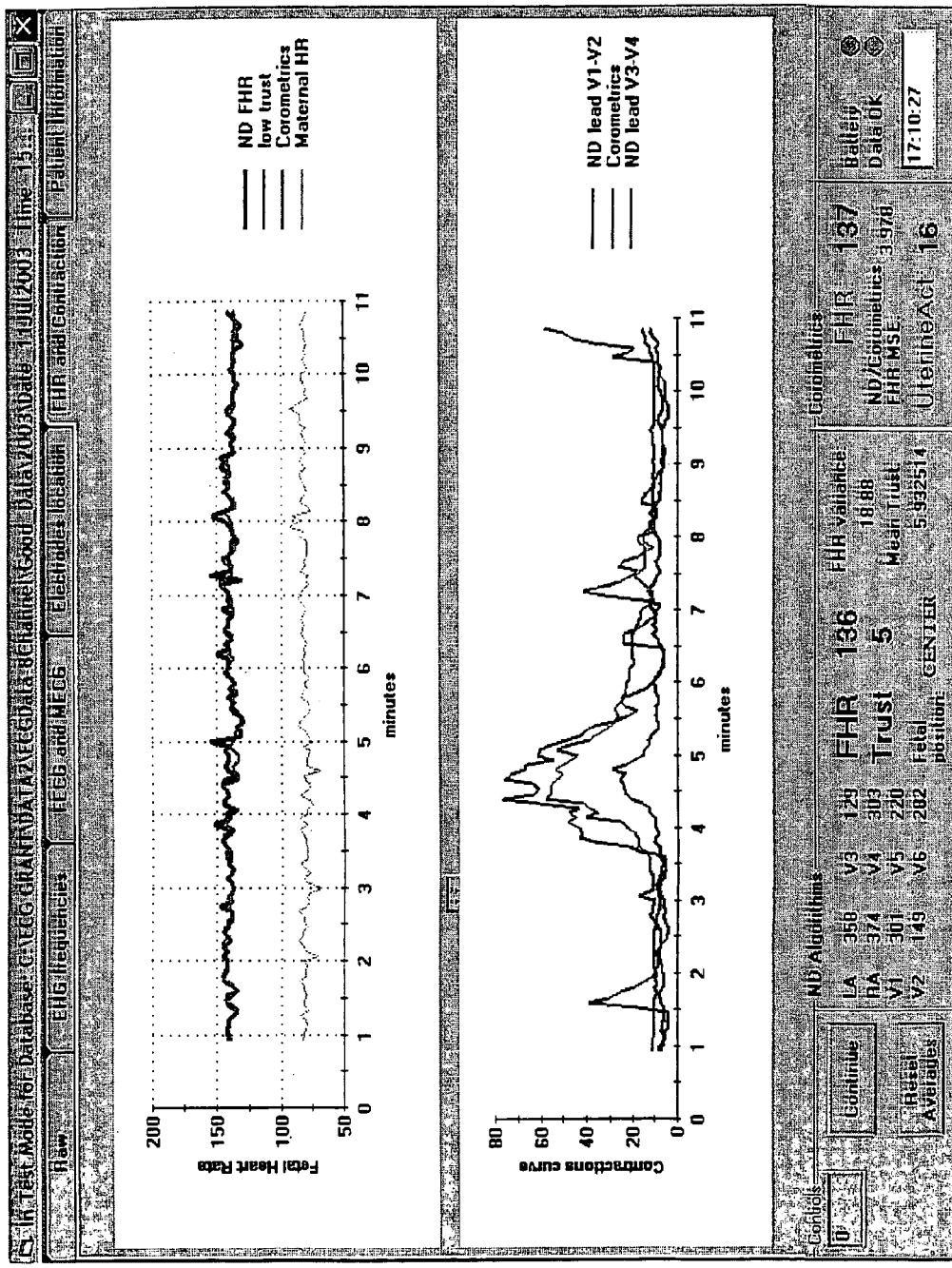
Figure 4F:
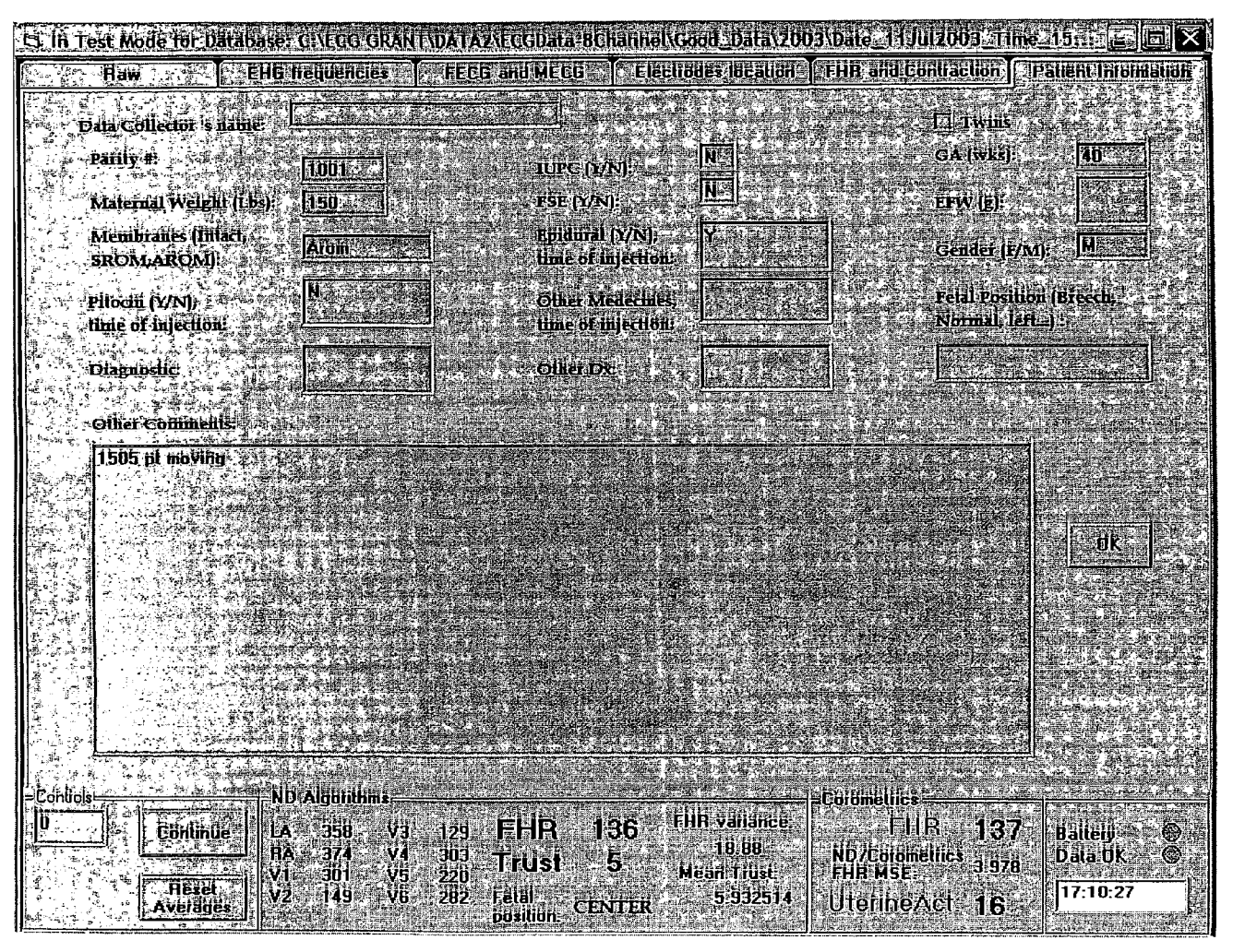

Advantageously, a browser or network interface is incorporated into the processing device to allow the user to view the processed data in a graphical user interface device, for example, a monitor. The results of algorithm operations of the subject invention can be displayed in the form of the interactive graphics, such as those illustrated in FIGS. 4A-4F. The user, whether it be a physician, a nurse, a technician, or a patient, can indicate the placement of the electrodes on the graphical maternal abdomen. In one embodiment, a graphical representation of the maternal abdomen is provided (see FIG. 4A) to track the location of the sensors (i.e., electrodes) as well as to indicate to the user whether optimal fetal signals are being detected by the sensors.

Software

Figure 5:
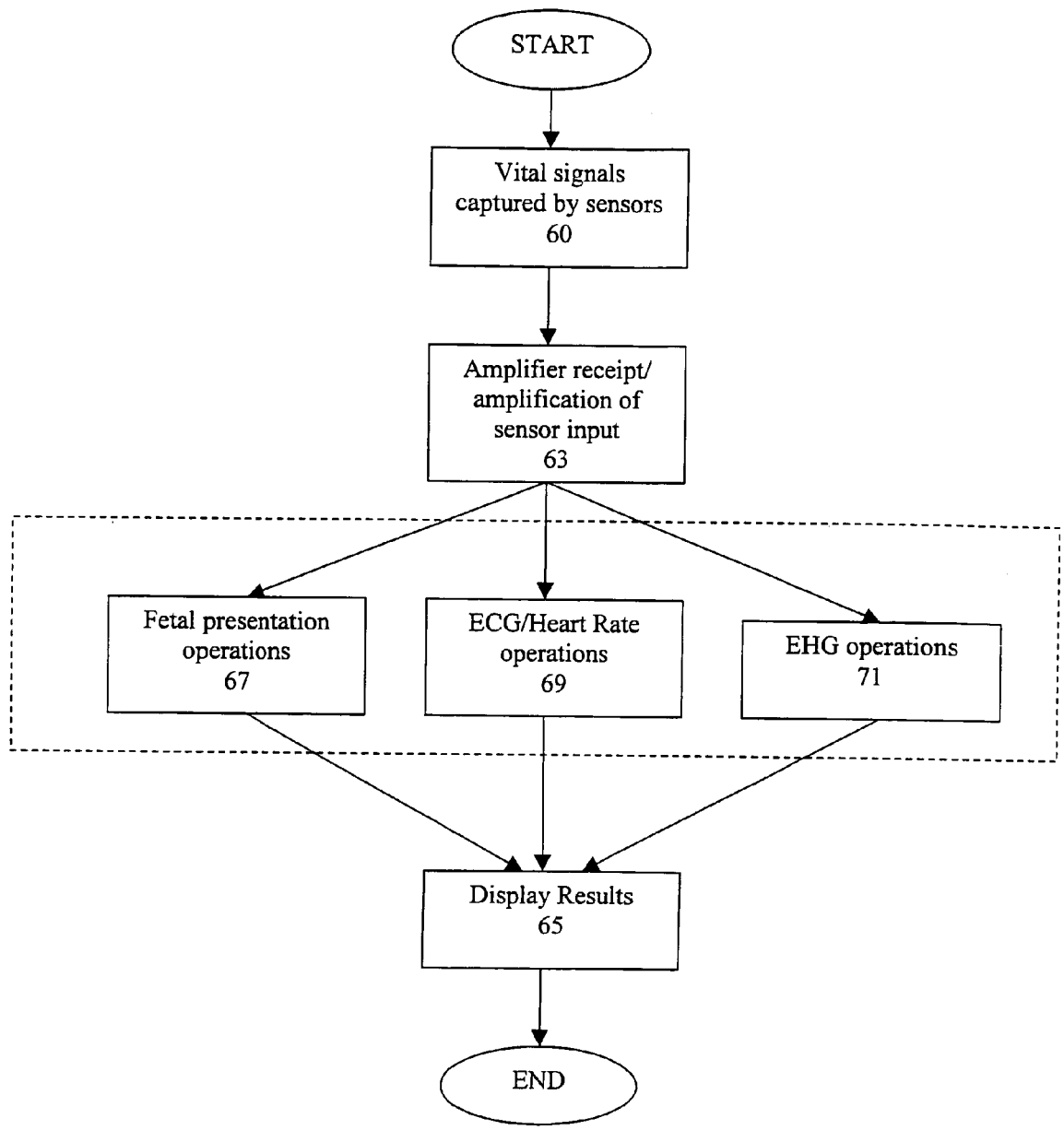
FIG. 5 illustrates a flow diagram illustrating steps for operating a maternal-fetal monitoring system of the invention.

The maternal-fetal monitoring system of the subject invention can function in a real-time setting to continuously provide accurate clinical data to the user. In operation, as illustrated in FIG. 5, maternal-fetal vital signals are captured by sensors 60 (raw signals) and input to an amplifier (i.e., raw signals) 63. Amplifier output is subsequently communicated to a variety of operational algorithms 36 for processing vital signals into clinical data and subsequent presentation of clinical data to the user 65. Operational algorithms 36 can include, without limitation, fetal presentation operations 67, ECG/heart rate operations 69, and EHG operations 71.

In certain instances, prior to vital signal processing, signals received from an amplifier are communicated to filter operations for each sensor channel. Raw signals extracted by sensors of the invention are a mixture of several sources, namely maternal-fetal vitals signs (i.e., maternal ECG, fetal ECG, EMG signals) and noise. In a preferred embodiment, each sensor channel is communicated to a corresponding band pass filter operation, which is accomplished on a computing means. According to the subject invention, a computer processor is used for filter operations as well as other processing functions.

In accordance with the subject invention, the filtered signals are then followed by appropriate operations for obtaining desired clinical data (i.e., ECG results (maternal and fetal); EHG results; a value to aid the user in assessing the quality of clinical data). Contemplated operations include, but are not limited to, ICA operations, EHG extraction operations; quality ("trust") factor operations; Pan Tompkins analysis operations; maternal-fetal channel determination operations; ECG waveform reconstruction operations; and fetal presentation-operations.

1—Independent Component Analysis (ICA) Operations

In accordance with the subject invention, filtered sensor output is communicated to ICA operators for each specific sensor channel used for ECG collection. ICA operators of the invention are preferably implemented in real time on a computing means (i.e., computer processor). The ICA operations place the filtered sensor output (i.e., mixture of signals from several sources—maternal, fetal and noise) into estimated independent components. In one embodiment, ICA operations are capable of calculating the estimated fetal ECG, estimated maternal ECG, and estimations of other noises in the filtered sensor output.

A variety of algorithms, known to the skilled artisan, are available for use in ICA operations of the subject invention. ICA (or blind source separation—BSS) algorithmic operations contemplated for use in ICA operations of the subject invention include, but are not limited to, Infomax ICA operations (Bell, A. and T. Sejnowski, "An Information-Maximization Approach to Blind Separation and Blind Deconvolution," *Neural Computation,* 7:1129-1159 (1995)); minimum mutual information operations (Comon, P., "Independent Component Analysis, A New Concept?" *Signal Processing,* 36(3):287-314 (1994)); maximum entropy and minimum mutual information operations (Yang, H. and S. Amari, "Adaptive Online Learning Algorithms for Blind Separation: Maximum Entropy and Minimum Mutual Information," *Neural Computation,* 9:1467-1482 (1997)); and Mermaid ICA operations (Hild, K. et al., "Blind Source Separation Using Renyi's Mutual Information," *IEEE Signal Processing Letters,* 8(6): 174-176 (2001)).

In a preferred embodiment, a Mermaid ICA algorithm is used in ICA operations of the subject invention. As known to the skilled artisan, a Mermaid ICA algorithm determines separate sources by minimizing the output mutual information. In one embodiment, the Mermaid ICA algorithm uses Renyi's entropy to estimate mutual information.

In certain embodiments, to simplify the computation of the gradient, a Mermaid ICA algorithm first projects the sources onto an orthonormal (whitened) space and then rotates these projections into a space of minimal mutual information. The projection is done with the well known Principal Component Analysis method. The rotation is done by adaptively updating the Givens angles. This update is done in an online manner by minimizing the mutual information between the outputs of the ICA algorithm.

The optimization steps are as follows: (1) initializing Givens angles (to all zeros or randomly); (2) computing the whitening matrix as prescribed using all samples in off-line separation/updating the whitening matrix using an adaptive principle components algorithm (PCA) in on-line; (3) using in off-line separation the batch gradient obtained by direct derivation of the optimal separation matrix parameters of the vector of Givens rotation angles, which is computed using all available samples; or, using in on-line separation, the stochastic gradient; and (4) updating the Givens rotation angles using the steepest descent. According to the subject invention, the use of a Mermaid ICA algorithm for ICA operations results in timely and accurate output.

2—Pan Tompkins Operations

In accordance with the subject invention, at the output of ICA operations, Pan Tompkins operations are performed on a computing means (i.e., computer processor). Pan Tompkins operations of the subject invention are based in part on a known, standard algorithm (the Pan Tompkins algorithm).

In one embodiment of the invention, the frequency bands of the Pan Tompkins algorithm are increased to higher frequencies and the lengths of the filters have been decreased. In a preferred embodiment, the following parameters of the standard Pan Tompkins algorithm are changed to fit the frequency range of fetal ECGs: (1) a band-pass filter; (2) a differentiation step (or function); and (3) a moving average step (function). More preferably, the parameters of the standard Pan Tompkins algorithm include the following: (1) a butterworth band-pass filter of order 6 and of pass band between 5 and 35 HZ is used; (2) a differentiation step of 5 point derivatives is used; (3) a moving average step following the squaring step uses a 20 point window.

The Pan Tompkins operations of the subject invention enable the detection of QRS complex peaks in the estimated maternal and fetal ECG signals (outputs of the ICA algorithm). In accordance with the subject invention, QRS complex location is used in calculating specific clinical data, namely fetal heart rate data.

In a related embodiment, Pan Tompkins operators perform computational analyses to provide clinical data such as RR intervals (defined herein as the time in seconds between 2 consecutive QRS peaks); instantaneous or beat to beat heart rate (HR)(60/RR); average HR, HR variance (which can be updated beat by beat); as well as estimated numbers of false positive and false negative QRS complexes. This clinical data (number of false positives, false negatives, etc.) can be input to maternal-fetal channel determination operators and/or quality ("trust") factor operators to determine which output channel is the fetal ECG and to determine the quality of the signal, respectively.

In accordance with the subject invention, preferably a false positive peak is estimated to be present when the RR interval between the previous peak and the present one is less than 70% of the average of the 5 previous RR intervals. Further, preferably a false negative according to the subject invention is estimated when the RR interval between the previous peak and the present one is greater than 130% of the average of the 5 previous RR intervals. Preferably, the average HR, HR variance, and number of false positive and false negative are calculated every 4 seconds.

3—Quality ("Trust") Factor Operations

In current monitoring systems, the signal separation performance cannot be directly measured because the actual original signals are not known. In contrast, the subject application enables determination of the quality of the separated signals (maternal versus fetal vital signals). In one embodiment of the invention, the quality of the ECG separation can be approximated by determining the properties of the ECG signals themselves. High quality ECG signals have high signal to noise ratios, clearly visible waveform characteristics typical of ECG waveforms, such as the P, Q, R, S, and T waves, and timing that is representative of the actual electromechanical beating of the heart. According to the subject invention, poor quality of signal separation indicates a great deal of noise whereas best quality of signal separation indicates any signal separation that is better than noise. For example, a quality of 0 is completely noise, a quality of 5 implies that the QRS waveform is clearly visible, repeatable, and much above the noise, and a quality of 7-10 implies that the P and T waves are visible.

The quality of the estimated fetal HR calculated from the fetal ECG and the quality of the fetal ECG signal itself, as extracted using the monitoring system of the subject invention, are directly related to the quality of the separation algorithm operations. There is currently no existing criterion for measuring the performance of separation algorithm (i.e., ICA or BSS) operations in environments where the mixing matrix is unknown (i.e., real data). According to the subject invention, a mechanism suitable for comparing the quality of separation algorithm operation performance on real data is based on an end-to-end system criterion (i.e., in terms of the real goals of the system).

Similarly, an EHG quality assessment (or trust factor) can be derived from the processed EHG signal based upon input variables corresponding to features that are characteristic of fetal or maternal EHG signals. In a preferred embodiment, the EHG quality assessment would be based on kurtosis, skewness, and the frequency components of the EHG signal. The kurtosis for the EHG should be approximately 8-10 for a 10-minute window. Skewness, a measure of symmetry, should be small indicating a symmetric EHG waveform. The EHG signal is also expected to have larger frequency components in the 0.1 to 0.5 Hz range.

Accordingly, a quality (or trust) factor (hereinafter referred to as "TF") can be provided using a TF operator of the subject invention, wherein the TF is based on intrinsic properties of the fetal ECG, HR, and/or EHG, and is used to enable the user to quantify signal separation success, automatic recognition of the maternal and fetal channels, and fetal ECG quality (i.e., from 0 (no separation, low quality) to 10). TF operations are performed on the output of Pan Tompkins algorithm operations and on the output of the ICA algorithm, described above, to provide to the user a numerical representation of the quality of the fetal ECG and heart rate values monitored using the system of the invention, which is useful in making diagnostic decisions.

In one embodiment, TF operations include the calculating for each signal at least one continuous probability function with at least one input variable. With the subject invention, these continuous probability functions, called Pf (fetal) and Pm (maternal), represent the probabilities that the output signal in question, found by the ICA algorithm, is respectively a fetal or maternal ECG and its corresponding HR, found by correlation and Pan Tompkins.

Preferably, the probability function is a Gaussian function. This simple mathematical form describes the probability of encountering any given error. As well understood by the skilled artisan, the Gaussian distribution has two free parameters per dimension: the mean and the standard deviation. According to the subject invention, these parameters (i.e., means and variances for each variable) can be fixed or variable. In one embodiment, these parameters can be determined individually or from a sample population.

Preferably, Pf and Pm consists of one or more of the following input variables corresponding to features that are characteristic of fetal or maternal ECG signals, respectively. These variables are compared to ideal values found for clean fetal or maternal ECG signals, or are compared to a combination of past values updated every 4 seconds. Preferably, these input variables include the following:

1. calculation of the estimated fetal heart rate with the autocorrelation function;
2. calculation of the estimated fetal heart rate with the Pan-Tompkins algorithm;
3. variance of the estimated fetal heart rate (from Pan Tompkins algorithm);
4. number of False Positives from Pan Tompkins algorithm;
5. number of False Negatives from Pan Tompkins algorithm;
6. the amplitude of the estimated fetal QRS peaks;
7. the ratio of the autocorrelation peak versus the variance of the autocorrelation function;
8. the sparsity of the estimated fetal ECG signal; and
9. mutual information. Mutual Information is calculated and minimized between the outputs of the ICA algorithm. The minimum value reached for a certain data set represents the quality of the separation and therefore can be used to determined separation quality.

In a preferred embodiment of the ECG trust factor, Pf and Pm have eight (8) input variables corresponding to features that are characteristic of fetal or maternal ECG signals, respectively.

Any one or combination of these input variables can be provided using processes as described below.

a) First, the average HR is calculated from the Pan Tompkins algorithm. For example, the average HR is the median value of the instantaneous HRs found by the Pan Tompkins operations during 4 seconds.

For the calculation of Pf, this average HR is compared to a combination of past values of the average fetal HR, hereinafter called FHRav. FHRav is initialized for all the patients to a value calculated from a sample patient population. By way of example, for a sample patient population of 100 patients, the average FHR was determined to be 145±35 bpm (beats per minute) with a variance of 20±20. This value is then updated every 4 seconds, depending on the previous FHRs found, which are calculated as a function of the trust factor, as described in the following formula:

$$FHRav = \frac{TF}{10} \times FHR + \frac{10 - TF}{10} \times FHRav.$$

When the extracted signal quality is very high, the trust factor is very high and FHRav tends to be equal to the currently found FHR. Likewise, when the trust factor is low, the current FHR is not trustworthy, so a longer term average is used. The HRs found at the end of the Pan Tompkins algorithm are compared to FHRav in the calculation of Pf. The closer the HR is to this value, the more probable the signal is the FECG.

For the calculation of Pm, the HR found is compared to the value of the maternal Heart rate (called MHRav) found by a correlation operation applied on the raw data. The average MHR and its variance can be calculated for each patient because signals corresponding to the maternal channel are easily extracted due to a high maternal influence in sensed signals. For example, unfiltered sensor signals can be passed through an autocorrelation function known to the skilled artisan, wherein overlapping windows of data are correlated to obtain the evolution of the heart rate over a selected period of time. For each autocorrelation signal, the highest peaks corresponding to ECG periodicity are detected and translated to a heart rate, which represents the average MHR, thus allowing for the calculation of the average MHR variance.

Preferably, an autocorrelation is performed on the signals closest to the maternal heart (typically RA, LA and v1, see FIG. 9) because these have the strongest maternal influence. A detection algorithm gives the location of the highest peak (beyond the DC offset) and therefore the average maternal RR interval and the average maternal heart rate. The three channels are then combined using a median function to prevent MHR errors caused if one electrode is disconnected or if any kind of problem arises on one or two electrodes.

b) The estimated variance of the HR is compared to a fixed value corresponding to the variance of the FHR/MHR found on a sample population. Preferably, the variance of the HR is compared to 25 in the calculation of Pf and to 4 in the calculation of Pm.

c) Next, the average amplitude of the detected QRS peaks in the output of ICA signal is calculated. The higher the amplitude of the peaks, the more probable the signal is an ECG signal.

d) An estimation of the number of correct beats not detected (false negative—FN); and an estimation of the number of incorrect beats detected (false positive—FP) is also computed from the peaks picked by the Pan Tompkins algorithm. The smaller these numbers are, the more probable the signal is an ECG signal. In a preferred embodiment, acceptable levels of FN and FP are less than 10%.

Also at the end of the ICA algorithm an autocorrelation is performed on the 4-seconds signals. For example, in the preferred embodiment where there are eight input variables, an autocorrelation is performed on eight 4-second signals. For each autocorrelation signal, a peak detection algorithm is performed to determine the highest non-DC peak. For an ECG signal, this peak corresponds to the average RR interval during the 4 second period, and therefore to the average HR (60/RR) during this 4 seconds period. From this autocorrelation method, several parameters are computed for the signals and serve as input to the probability functions:

1. The average HR (which can be determined by using the autocorrelation method described above). If the signal in question is not an ECG signal, this value is not representative of a HR. The closer this HR value is to the previous ECG HR value, the higher the TF will be. The HR is compared to FHRav in the calculation of Pf and to MHRav in the calculation of Pm.
2. The variance of the autocorrelation in between peaks. If the noise level in the signal is low, this value will be low. The lower this value is the higher the trust factor will be,
3. The amplitude of the peak in the autocorrelation function is compared with the variance of the autocorrelation function. The higher this ratio is the higher the TF will be.

Since the ECG signal is characterized by a QRS spike that is significantly larger than the rest of the signal, the sparsity of the ICA output signal is also used as a criterion to determine if it is an ECG signal. The percentage of signal data-points that are less than half of the peak value will be very large in an ECG signal, therefore this parameter is entered into the probability equation.

Another preferred measure of sparsity is Kurtosis. Kurtosis is defined as the normalized fourth central moment of a distribution X:X:

$$\text{kurtosis}(X) = \frac{E[(X - \mu)^4]}{\sigma^4}$$

where $\mu$ is the mean and $\sigma$ the standard deviation of the distribution X. ECG signals typically have a kurtosis much greater than 4 and the noise signals typically have a kurtosis value close to 3 (the kurtosis of the Gaussian distribution). Experimentally, it was verified that for a signal to noise ratio (SNR) greater than 4 dB, FECG and MECG can be clearly identified only by using the kurtosis of the signal.

Mutual Information is calculated and minimized between the outputs of the ICA algorithm. The minimum value reached for a certain data set represents the quality of the separation and therefore can be used to determine separation quality.

In the preferred embodiment, an additional test is performed after the Pan-Tompkins algorithm. In the case where the MHR and the FHR are very close, it is desirable to be able to distinguish the fetal ECG (FECG) and the maternal ECG (MECG) (and therefore the FHR and the MHR). A precise value for the MHR is easy to determine from the raw signal, and therefore the MECG at the output of the ICA algorithm is easy to recognize. From the MECGs, the Pan-Tompkins algorithm gives us the location of the MECG QRS peaks. To detect the fetal channel, the signals that have their QRS peaks at the same location (within a few points range) as the MECG QRS peaks are eliminated. Pf is brought to 0 for these signals.

TF operation in accordance with the subject invention provides the user with a means for assessing the performance and reliability of ICA operations output.

Figure 6:
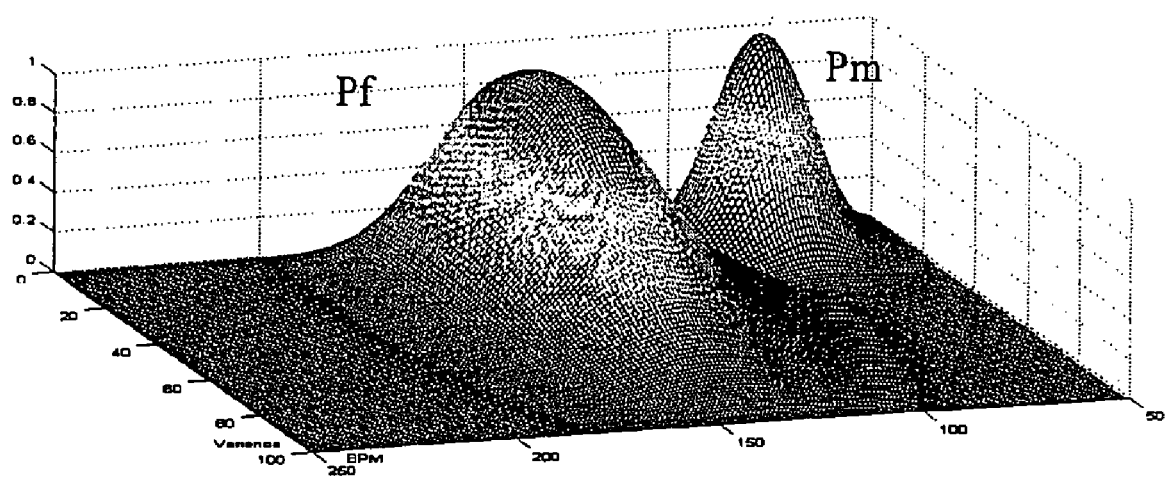
FIG. 6 is a graphical illustration of the probability of a vital signal being from the mother and the fetus, as extracted by the monitoring system of the invention.

In one embodiment, the probability functions for a specific channel (kChan) are defined by the following mathematical and operational relationship: The associated Gaussian distribution curve is provided in FIG. 6.

$$Pm^1 = e^{-0.5\{(\frac{HR1-MHRav}{10})^2+(\frac{HRvar1-4}{10})^2+(\frac{AmpPeak-10}{10})^2+(\frac{FN+FP}{10})^2\}}$$

$$Pf^1 = e^{-0.5\{(\frac{HR1-FHRav}{20})^2+(\frac{HRvar1-25}{20})^2+(\frac{AmpPeak-8}{10})^2+(\frac{FN+FP}{10})^2\}}$$

$$Pm^2 = e^{-\left(\frac{HR2-MHRav}{\sqrt{2}\times 10}\right)^2 - \left(\frac{sparsity-750}{\sqrt{2}\times 10}\right)^2} \frac{1}{2}\log(1+0.3r)$$

$$Pf^2 = e^{-\left(\frac{HR2-FHRav}{\sqrt{2}\times 10}\right)^2 - \left(\frac{sparsity-700}{\sqrt{2}\times 10}\right)^2} \frac{1}{2}\log(1+0.3r)$$

$$Pm = \mathrm{Max}(Pm^1, Pm^2)$$

$$Pf = \mathrm{Max}(Pf^1, Pf^2)$$

where:
e is the exponential operator;
HR1 is the heart rate calculated for each sensor channel during Pan Tompkins operations;
HR2 is the heart rate calculated for each sensor channel during the autocorrelation operations;
MHRav is the average maternal heart rate;
FHRav is the average fetal heart rate;
HRvar1 is the variance in HR;
FN is the estimated percentage of number of correct beats not detected;
FP is the estimated percentage of number of incorrect beats detected;
AmpPeak is the amplitude of the ECG QRS peaks;
sparsity is the number of points in the signal that are situated below 50% of the maximum (measure of the sparsity of the signal); and
r is the ratio between the amplitude of non-DC peak in the autocorrelation function; and the variance of the autocorrelation function.

In another embodiment, the input parameters are used to create membership functions based on the principles of fuzzy logic. Each parameter is compared to the expected value of the parameter and the membership function determines the probability that this parameter is consistent with the appropriate ECG signal. A membership function for the Kurtosis parameter is:

$$e^{-0.5 \cdot \frac{(x-MEAN)^2}{STDDEV^2}},$$

, where the MEAN is the sample mean for the parameter of interest and the STD DEV is the sample standard deviation of the parameter of interest. Au example of the membership function for the Kurtosis parameter is:

$$Pf_1(x) = e^{-0.5 \cdot \frac{(x-8.1)^2}{1.8^2}}$$

-continued $$Pm_1(x) = e^{-0.5 \cdot \frac{(x-22.9)^2}{8^2}}$$

One or more of these membership functions are then combined to create an overall probability for the selection/quality assessment of each channel. This combination can be done in multiple methods, but in this embodiment one of the standard fuzzy logic techniques is used:

$$Pf = \min_i(Pf_i) \text{ and } Pm = \min_i(Pm_i), i = 1, 2, 3 \ldots .$$

According to the subject invention, at the output of the ICA algorithm and Pan Tompkins algorithm operations, TF operations are performed on estimated signal results. TF operations include computing the probabilities for Pf and Pm, see FIG. 6; and comparing the two probability values to classify whether the signal result is a maternal signal (i.e., maternal ECG), a fetal signal (i.e., fetal ECG), or other signal such as noise.

In certain embodiments, a TF is computed by truncating the value of 10 times the highest probability Pf. It ranges from 0 to 10 (where 10 corresponds to a probability of 1). 0 is the worst case where the signal is very unlikely to be a fetal ECG and is most-likely noise. 10 is the best case where the fetal ECG is well detected and the value of the heart rate that is calculated using Pan Tompkins operations is an accurate value.

4—Maternal-Fetal Channel Determination Operations

The output signals of ICA operators are generally of arbitrary scale and order. In addition, as the signal changes, the location of the fetal signal channel is likely to change as well (i.e., during contractions, the contraction signals become larger and produce different overall signal characteristics, both raw and separated). Thus, detecting which channels are maternal ECG, fetal ECG, and noise is beneficial to the user. Currently, channel classification is a complex task normally performed manually by skilled clinicians. The subject invention advantageously provides automatic, real-time classification of maternal and fetal output channels to enable appropriate processing algorithm operations, such as those described above, on desired signals.

Maternal-fetal channel determination operations are performed on the TF operator(s) output. TF operator(s) output is processed by maternal-fetal channel determination operator(s) to identify the highest Pm and Pf values, which corresponds to the probability of the signal being a maternal or fetal signal channel, respectively. In a preferred embodiment, a signal is classified as a maternal signal when Pm>Pf and Pm>0.7. On the remaining signals (not classified as maternal signal), the signal with the highest Pf is classified as a fetal channel.

For cases where the FHR and the MHR are very close, the location of the QRS peaks is an important source of information to differentiate the two signals, since it is very unlikely that the fetal and maternal waveforms will be synchronized totally. The locations of the maternal QRS peaks are found in the electrodes closest to the maternal heart and with the Pan-Tompkins method, since the maternal ECG is very strong in these channels. At the output of the Pan-Tompkins algorithm, all the signals that have QRS peaks at the same location as the MECG (with 20 ms precision allowed) are eliminated by bringing their membership functions to zero.

5—EHG Extraction Operations

According to the subject invention, EHG extraction operations comprise (1) down-sample operator(s); (2) filtering operator(s); and (3) contraction detection operator(s). Any signals from sensors of the invention can be used in EHG extraction operations. In a preferred embodiment, signals from sensors located along the vertical midline of the maternal abdomen are input to EHG extraction operator(s).

Because EHG signal frequencies are often in a low frequency range (<5 Hz), input signals received from an amplifier (and A/D converter) are communicated to down sample operator(s) to remove extraneous high-frequency information. For example, where signals from eight channels (see FIG. 1, sensors 1$a$-1$d$) are sampled originally at a frequency of 200 Hz, the down sample operator(s) reduces the sample rate to 20 Hz. The down-sampling of the EHG is desired so as to reduce the volume of data to be processed by the computing means. In addition, at the output of the down-sample operator(s), a non linear operator can be performed on a combination of the down sampled signals. Preferably the nonlinear operator is the absolute value operator and the combination of channels is a pair wise difference:

$1_{ab}=|1_a-1_b|$; and $1_{cd}=|1_c-1_d|$.

These operator(s) output (absolute values of $1_{ab}$ and $1_{cd}$) are communicated to filtering operator(s) to obtain the envelope of an EHG wave. Known digital filters can be used to perform EHG extraction/filtering operations. In one embodiment, a low pass Butterworth filter (i.e., of order 4, having a cut off frequency 0.05 Hz) is used to obtain the envelope or slow wave of at least one EHG wave.

Output from filtering operator(s) is input into contraction detection operator(s) to detect the beginning, end, duration and amplitude of a uterine muscle contraction. The contraction detection algorithm operation relies on identifying those segments in the EHG results that have values exceeding a particular threshold level for a specified duration. In order to determine the threshold, the contraction detection operator(s) analyze filtering operator(s) output signals using a specified time frame (or window). In one embodiment, filtering operator(s) output signals are analyzed by contraction detection operator(s) in 4 minute wide windows, with 1 minute shifts.

According to the subject invention, with every contraction detection operation, the signal samples (filtering operator(s) output) in a window are processed to obtain a basal tone and a threshold for normal versus contraction activity. To determine the threshold for detection of contraction changes, contraction detection operator(s) add 25% of the windowed signal range to the basal tone. Thus, the threshold for detection of contractions can change according to the signal level. In accordance with the subject invention, a contraction can be recognized if the duration of an EMG result is greater than a set period of time (i.e., 30 seconds) and the amplitude is greater than a percentage over the threshold value.

Contraction determination operations of the invention also include determining the intensity of contraction, which represents the number of spikes during every uterine contraction. Contraction intensity determination, as performed by contraction-determination operator(s) of the invention, requires estimation of the timing parameters (starting time and duration) of the contraction signal. In accordance with the subject invention, to determine contraction intensity, filtering operation output (high frequency signal, $1_{ab}$ and $1_{cd}$) is input to another filter operator(s) to smooth (i.e., remove high frequencies) the paired sensor signals. In one embodiment, the sensor signals are smoothed by a low pass Butterworth filter ($4^{th}$ order) with cut off frequency 0.4 Hz. After "smoothing", the contraction determination operator(s) determine the number of positive peaks in each contraction. Only those contraction signal peaks having width greater than 2 seconds and amplitude greater than 25% of the contraction amplitude are analyzed.

Further, according to the subject invention, EHG extraction operation includes providing an EHG spectrogram and contraction curve. In one embodiment, the EHG spectrogram and contraction curve are plotted on a graphical user interface of the invention. In a preferred embodiment, the contraction curve is plotted below the fetal heart rate and maternal heart rate trace. It has been conjectured in the literature that contraction efficiency may be determined with appropriate analysis of the frequency content of the EHG signal. Moreover, spectral characteristics of the EHG curve may be able to be used to predict contraction efficiency and preterm labor. Accordingly, the present invention can convert EHG signals into values proportional to the pressure in the uterus (i.e., IUPC) or directly to montevideo units, which to date has not been contemplated for monitoring systems. In further embodiments, the present invention utilizes neural network systems to convert EHG signals into Montevideo units.

The frequency content of the EHG, as typically shown in a spectrogram such as those illustrated in FIGS. 4B-4E, and other results provided by EHG extraction operations can aid the user in estimating or be used to determine contraction effectiveness, detecting false versus real labor (i.e., useful in saving trips to the hospital for Braxton Hicks contractions), probability of vaginal delivery (or conversely, the need for a C-section), time to delivery, arrested descent, uterine rupture, and labor progress. As described above, this system could be used as a home monitoring system that not only continuously monitors fetal heart rate and ECG to detect fetal well-being, but also can be used to determine the difference between effective and non-effective contractions and false versus real labor.

In addition, the electrical signal from the abdomen (the EHG coupled with the EMG of abdominal muscles) could be used as a biofeedback mechanism to help direct maternal pushing effort during the second stage of labor. Such feedback may be particularly helpful when neuraxial analgesia has blunted sensation from the abdomen and perineum.

6—ECG Waveform Reconstruction Operations

It is well understood by the skilled clinician that heart defects can be detected by analyzing the different intervals and segments of ECGs. To determine normal ECG values for the fetal heart, which is applicable to fetal health (and heart health) during pregnancy or labor, more than the location of the heartbeat (the QRS segment) might be required. For example, the lower frequency attributes of the ECG signal, such as the P and T waves, can be useful in determining fetal heart standards, the early diagnosis of fetal heart defects, as well as establishing fetal health.

At the output of ICA algorithm operations, different signals may have been distorted by different filtering operations (i.e., including preprocessing filtering with the amplifier). For example, ICA operations output often include fetal ECGs having P and T wave amplitudes comparable to the noise amplitude. This makes these waves difficult to detect. State of the art monitoring systems are unable to provide accurate fetal ECG waveforms (including lower frequency P and T waves) as well as to eliminate the high frequency noise and the base line wander. Normally, P and T wave frequencies are in the 1 to 5 Hz range for the maternal ECG and from 2 to 10 Hz for the fetal ECG. The base line wander is in the 0 to 3 Hz range and the high frequency noise, mainly due to the power line interference is approximately 60 Hz.

Generally, the QRS peaks of ECG results are generally visible post ICA operations. However the fetal ECG signal output of ICA operations is commonly unrecognizable as an ECG signal by skilled physicians, who are accustomed to observing clean adult ECGs.

In accordance with the subject invention, in certain embodiments of the monitoring system it is desirable to reconstruct a "reshaped" fetal ECG source. In one embodiment of the invention, at least one known filter is used to perform ECG waveform reconstruction operations on ICA operations output. In a related embodiment, an inverse filter and then a band pass filter are used by ECG waveform reconstruction operator(s) to reconstruct and highlight the different waves present in ECGs signal/ICA operations output (in particular fetal ECG signals) while removing high frequency noise and base line wander.

In a preferred embodiment, the following inverse filter operator (used in ECG waveform reconstruction operations) is defined by the inverse of the preprocessing filter: $H(z)=1/(1-0.99z^{-2})$.

The band pass filters used in ECG waveform reconstruction operations are FIR filters. In a preferred embodiment, for the maternal ECG signal, an FIR filter of order 40 and of band [2 Hz, 50 Hz] is used. For the fetal ECG signal, an FIR filter of order 30 and of band [5 Hz, 50 Hz] is used. According to the subject invention, the fetal ECG (and maternal ECG) waveforms can be plotted on a graded figure so as to enable the user to extract the different ECG intervals and segments that are useful in diagnosis/determining clinical strategy. Similarly, the ECG intervals can be calculated automatically by the processing means.

As described above, further embodiments of the invention provide a computing means that includes a storage means. The storage means can collect and/or display via the graphical user interface, ECG waveform reconstruction operations output (i.e., ECG reconstructed waveforms having both P and T waves) as well as ICA operations output (i.e., ECG with highlighted QRS spikes and P and T wave removal with other noises).

In certain embodiments, the invention provides a software means for analyzing reconstructed ECGs, in particular, the fetal ECG. The reconstructed fetal ECG can be used to diagnose fetal acidosis and cardiac arrhythmias.

7—Operations for Determining Fetal Heart Electrical Influence in Different Sensors During the first two trimesters of gestation, the fetoabdominal volume conductor can be considered as a homogenous volume conductor and therefore the closer the electrode is to the fetal heart the higher the amplitude of the fetal ECG signal from the sensor(s). According to the subject invention, the location of the sensors (i.e., electrodes) corresponding to the highest coefficients provides the user with the location of the fetus in the uterus (low, high, right, left). The electrodes corresponding to the lowest coefficients can be moved to the region where the fetus is located in the abdomen to obtain raw signals with higher fetal influence (thus improving system performance).

From the $27^{th}$ to the $37^{th}$ weeks of gestation, a highly resistive layer surrounds the fetus: the vernix caseosa. Measurements confirm the model with a high resistivity layer (vernix) with 2 holes that are situated on the vertical axis. The two most probable pathways are the oronasal cavities situated over the head of the fetus and the umbiliculus situated at the other end of the fetal torso. During this period the current flows are not transmitted homogeneously within the abdomen and the influence of the fetal ECG in the different sensor channels may not correspond to the fetal position in the uterus. However the user can still move the sensors, which have been determined to have low fetal influence using operations described below, to better locations on the maternal abdomen.

In accordance with the subject invention, the ICA algorithm operations performance (i.e., as quantified by TF output) depends on the quality of the raw signals and the relative amplitude of the fetal ECG in the raw data (prior to filtering operations). Accordingly, ICA algorithm operations output is a function of sensor position. The following operations for determining fetal heart electrical influence in sensors include the function of optimizing ICA algorithm operator(s) output.

Figure 7:
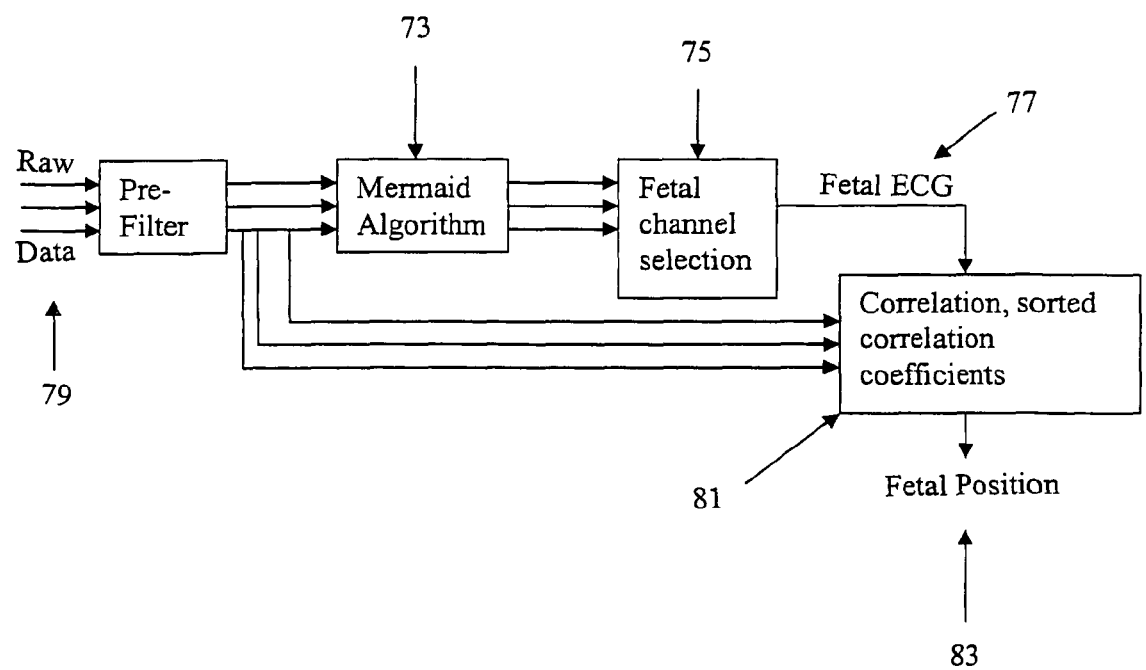
FIG. 7 is a flow diagram illustrating steps for determining the fetal heart electrical influence on different sensors, in accordance with the system of the invention.

Operations for determining fetal heart electrical influence in sensors of the invention include input-output matching for correlating ICA operator(s) output with raw sensor input (i.e., non-filtered sensor input), see FIG. 7. For example, at the output of ICA algorithm 73 and maternal-fetal channel determination 75 operations, the estimated fetal ECG signal 77 (or a projection of this fetal ECG signal based on the orientation of the electrodes and fetus) can be correlated 81 with the original, raw sensor signal channels 79. The resultant correlation coefficients correspond to the influence of the fetal heart electrical influence in the different electrodes, and are provided to the user. Further, the correlation coefficients can be used in presenting to the user fetal position 83.

Assuming the relationships between signals are linear, correlation techniques determine if a sensor signal output "resembles" another signal output, since these methods detect linear dependencies between signals. However, the linear dependency assumption is simplistic in the case of real data. Mutual information (MI) is a measure of dependencies (linear or non-linear) between signals. MI is null when the signals are independent. Thus, as the MI value increases, the strength of the dependency between the signals increases accordingly. With such cases, instead of simple correlation between the output of the ICA and the raw data, the input-output matching means can include calculating the mutual information value between the signals to find out the influence of the fetal signal output in each raw signal.

Alternatively, input-output matching means can be provided using non-linear matching methodologies. Neural network systems are non-linear adaptive systems that can detect non-linear dependencies between signals. Using a filtered version of the output of the ICA algorithm as a template and neural network, the influence of the fetal electrical activity in the different channels can be determined.

In certain situations, the ICA algorithm operator(s) output may not be optimal and/or the estimated fetal ECG may not be extracted. Although correlation of the estimated ECG signals and the raw signals can still be calculated, since the fetal channel may not contain any actual fetal ECG signal, the correlation coefficients may be skewed. To address this possibility, the subject invention correlation is performed based on TF operations output. For example, since the trust factor operations output quantifies the performance of ICA algorithm operations, when TF operations output is lower than a set value, correlation calculation is not performed and the user is notified. In a preferred embodiment, a user is notified that correlation calculations will not be performed when TF operations output is lower than 2. The user can then change the position of the electrodes to obtain better signals (or correlation coefficients).

In one embodiment, the position of the electrodes is provided to the user on a graphical user interface. In the graphical user interface, a page is created to allow the user to display the placement of the electrodes on the maternal abdomen (i.e., on a drawing). Where a set of electrode on a mesh is used, the position of the electrodes is always known and recognized by the computing means.

Using the correlation coefficients provided by operations for determining fetal electrical heart influence in the sensors enables the user of the invention to fine tune the sensor placement for better signal positioning.

8—Fetal Presentation Operations

Fetal presentation impacts labor and delivery with the potential for prolongation of labor, increased pain and/or labor dystocia (inability to deliver vaginally) and possibly fetal distress and complications. While fetal presentation is normally determined by palpation of fetal parts through the maternal abdomen, accuracy depends on the skill of the examiner, as well as the girth of the patient. During labor the cervical examination can help identify the orientation of the fetal head (or presence of a different presenting part, e.g., foot or buttocks), but again depends on the skill of the examiner and the quality of the examination (dilation of the cervix, etc.). When doubt remains, ultrasound can usually identify the fetal presentation, if not the orientation of the presenting part (e.g., occiput direction). However, a routinely applied monitor that alerts the clinician to an abnormal presentation early on may reduce complications. For example, if a breech position is detected, either an external cephalic version (flipping the baby over) attempted, or elective cesarean delivery.

As known by the skilled artisan, different signals from different sensors placed on the maternal abdomen represent different projections of the fetal heart vector. As understood by the skilled clinician, different waveforms of fetal ECG signals have different shapes depending on the location/orientation of signal collection. In one embodiment of the invention, models of the fetal heart vector for different fetal presentations are created and the models are projected onto the 8 different signals (often called leads) to assess the quality of sensor placement. Templates of simulated fetal ECG waveforms corresponding to different fetal presentation in the uterus are then presented to an input-output matching means. In one embodiment, each template is correlated (or "matched") with the raw data at the location of the fetal QRS complex. Accurate fetal presentation is provided by the highest correlation coefficient.

As known to the skilled clinician, the heart possesses an underlying activation structure that serves the mechanical function of the heart as pump. The anatomy of the fetal heart differs from the adult heart in its mechanical functioning. As oxygen is supplied to the fetus by the placenta, the need for pumping blood through the lungs is not there. Postnatally, the left ventricle of the heart is pumping blood to the body and the right ventricle blood to the lungs. In the fetus both ventricles pump blood primarily to the body.

Figure 8:
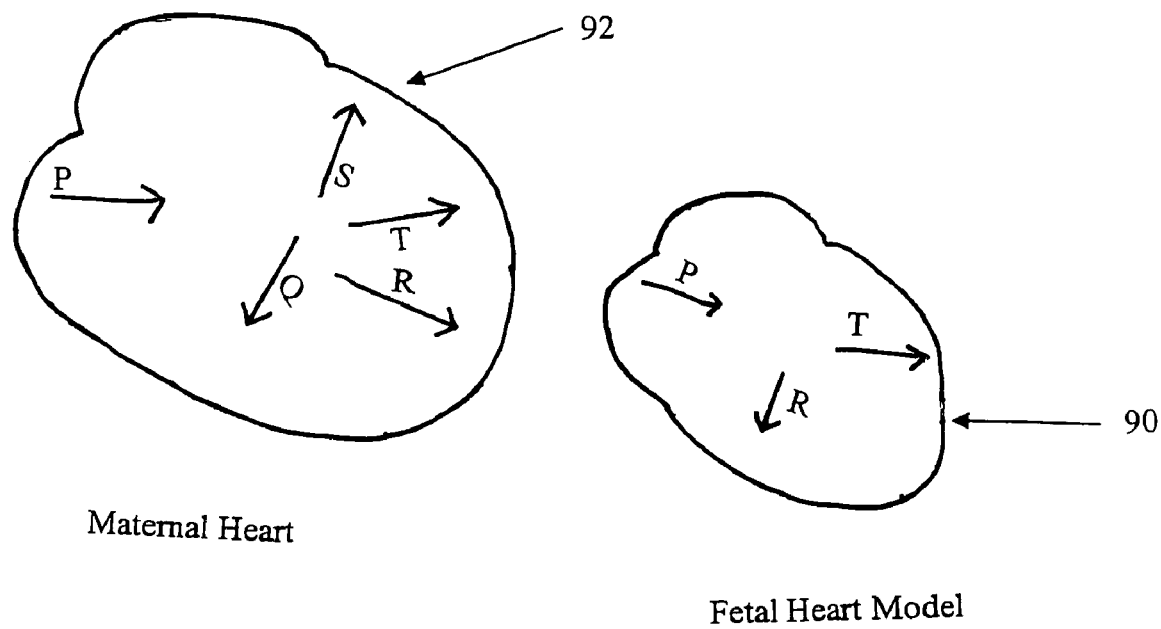
FIG. 8 illustrates models for fetal heart vectors and maternal heart vectors in accordance with the subject invention.

As illustrated in FIG. 8, the maximum amplitude of the QRS complex for fetus and young children 90 is found when it points to the right-anterior inferior octant, whereas for adults it is rotated over 90 degrees and points to the left. For the P wave, in general, the same direction is observed in the fetal heart as in the adult heart 92, pointing from the right to the left atrium. Data (as collected from newborns) show that it is likely that both P and T waves point in more or less the same direction and the R peak is more or less under an angle of 90 degrees with these other two. In this configuration, it is primarily the QRS complex that shows a different direction in the fetal case 90 when compared to the adult case 92.

In one embodiment of the invention, it is assumed that the dipole model of the postnatal case resembles the prenatal case. The amplitude of the dipole representing both P and T wave is about one sixth of that of the QRS complex.

Depending on the fetal presentation as determined using operations described below, the fetal heart vector model has to be rotated. Then fetal presentation operator(s) project the different wave vectors onto the basis made by the different sensors (i.e., 8 electrodes of FIGS. 1 and 2) and a simulated fetal QRS complex for each electrode is obtained.

Figure 9A:
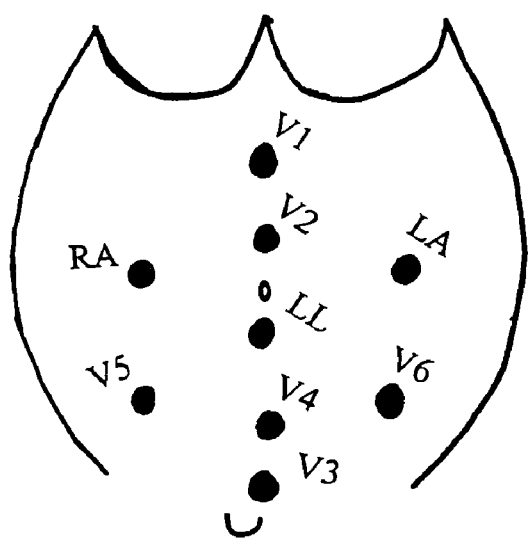
FIGS. 9A-B illustrate an example of a vertex presentation as provided by the subject invention when using sensors positioned on a mesh as provided in FIG. 2.
Figure 9B:
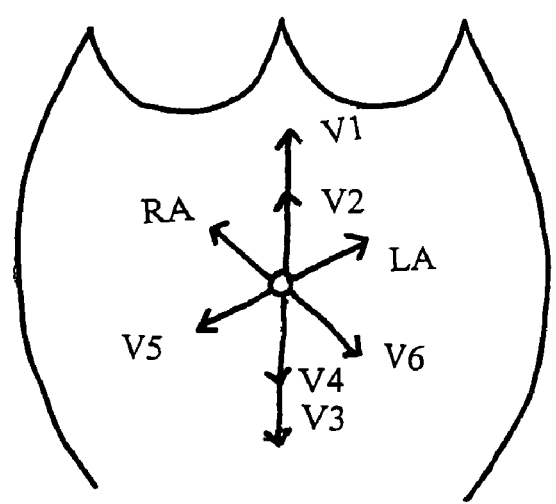
Figure 10:
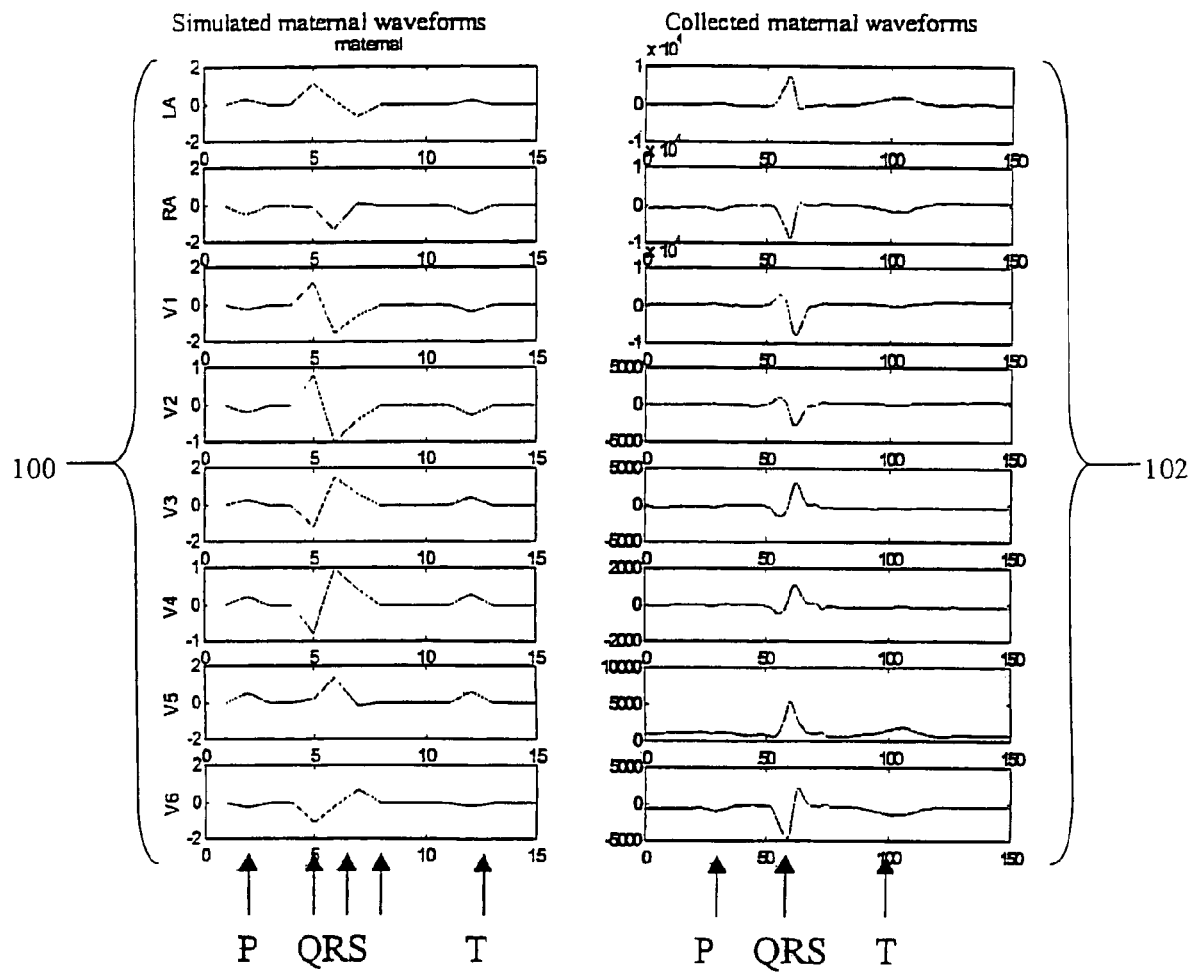
FIG. 10 is an illustration comparing simulated ECG waveform versus collected ECG waveform for each electrode ($V_{1-6}$, RA, and LA).

The electrodes ($V_1$, $V_2$, $V_3$, $V_4$, $V_5$, $V_6$, RA, and LA) are positioned on a maternal abdomen in FIG. 9A using a mesh as seen in FIG. 2. With a sensor-mesh, for pregnant women without heart problems or diseases, the shape of ECG waveforms should be similar to a template of simulated maternal waveforms, as long as the sensor positions remain unchanged. An example of a model for vertex presentation using the electrodes of FIG. 9A is provided in FIG. 9B. FIG. 10 shows maternal simulated ECG waveforms for each electrode 100 in comparison against the actual, collected waveforms for each electrode 102.

Figure 11:
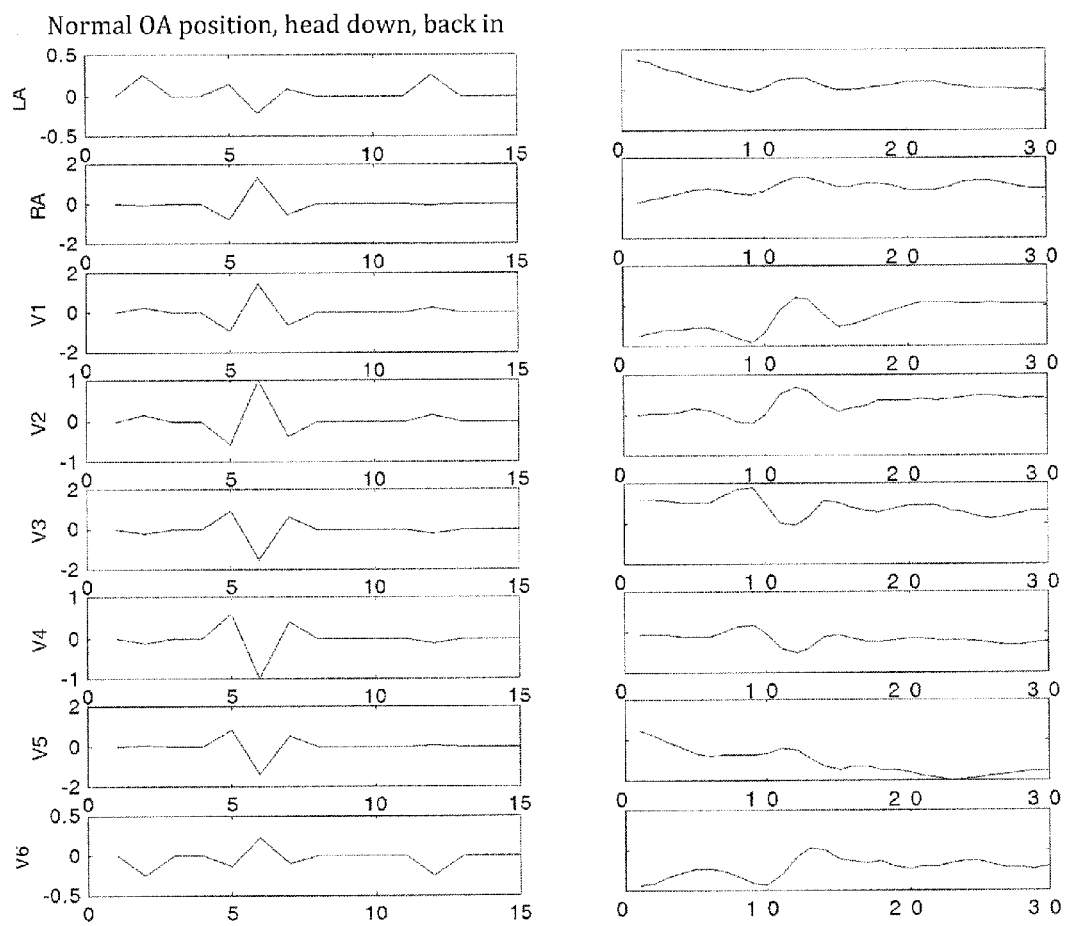
FIG. 11 illustrates a simulated fetal ECG waveform for a specific fetal position as compared to collected ECG waveform for each electrode ($V_{1-6}$, RA, and LA).

As described above, fetal ECG waveforms depend on the fetal presentation. FIG. 11 shows the simulated fetal ECG waveforms 104 that should be obtained with the sensors placed in positions as described in FIG. 9 when the fetus is in a normal OA position, head down, back in front. As illustrated in FIG. 11, the collected ECG waveforms 106 substantially correspond to the simulated ECG waveforms 104, wherein most of the differences can be attributed to a mixture of noise and maternal ECG.

Figure 12A:
FIGS. 12A-C illustrate various templates corresponding to different fetal presentations in the maternal abdomen that are provided in accordance with the present invention.
Figure 12B:
Figure 12C:
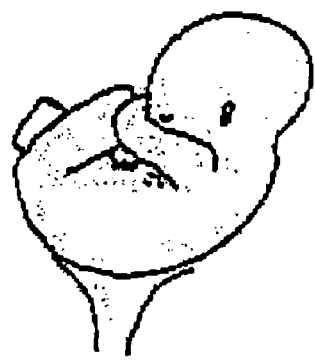

In accordance with the subject invention, a variety of templates corresponding to different fetal presentations can be provided and correlated with the collected waveforms and the template that provides the highest correlation coefficient corresponds to the estimated fetal presentation. The following are different templates of the invention, without limitation: Vertex (96.8% of pregnancies) as illustrated in FIG. 12A; Breech (2.5% of pregnancies) as illustrated in FIG. 12B; and Shoulder (0.4% of pregnancies) as illustrated in FIG. 12C.

8—Intra-Uterine Pressure (IUP) Operations

Mechanical contractions are the manifestation of the cyclic polarization and depolarization of the uterine muscles. The spontaneous electrical discharge in the muscle from the uterus consists of intermittent bursts of spike discharges (action potentials), characterized by slow and fast waves. The slow wave is associated with the appearance of bursts while the fast wave determines the rate of firing of individual spikes within the bursts, and hence represents the contraction intensity. This electrical activity of the uterus increases the intrauterine pressure, thereby exerting force on the abdominal wall inducing mechanical contractions.

In certain embodiments, non-invasive and real-time estimation of intra-uterine pressure (IUP) can be determined using a means for estimating intra-uterine pressure. In certain embodiments, the means for estimating IUP includes software analysis of EHG extraction operations output. In other embodiments, a neural network (or other intelligence methods) system is provided to analyze EHG extraction operations output to determine IUP. According to the subject invention, a multi layer perceptron (MLP) can be used to estimate the IUP signal from the EHG, wherein the frequency information in the EHG from EHG extraction operations output is used. In a preferred embodiment, the MLP can be trained with an error that is weighted more heavily during contractions. In an additional embodiment, a signal derived from the EHG can be extracted that is not identical to the IUP signal, but yet contains clinically relevant information that can be used in lieu of the IUP signal.

In accordance with the subject invention, an extracted signal derived from the EHG that contains clinically relevant information that can be used in lieu of the IUP signal (also referred to herein as the "IUP-like signal") can be used for a variety of purposes. For example, the IUP-like signal can be used to evaluate labor progression including evaluating contraction efficiency, the effectiveness of drugs used to induce labor, likelihood of labor dystocia, and/or to provide feedback as to the effectiveness of maternal expulsive efforts.

In a related embodiment, EHG extraction operations or IUP-like signals can be used during the post-partum period.

In one embodiment, the spectrogram of the EHG data set is computed over a window of 2000 samples and is divided into 18 different bands of frequencies ranging from 0-100 Hz. The average energy in every frequency bin (i.e., 18 frequency bins) for the 8 channels is given as input to a neural network system (144 inputs). The window is shifted by 100 samples and the spectrogram computation is repeated. Thus the input to the MLP is the evolution of frequencies in the EHG over time.

Figure 13:
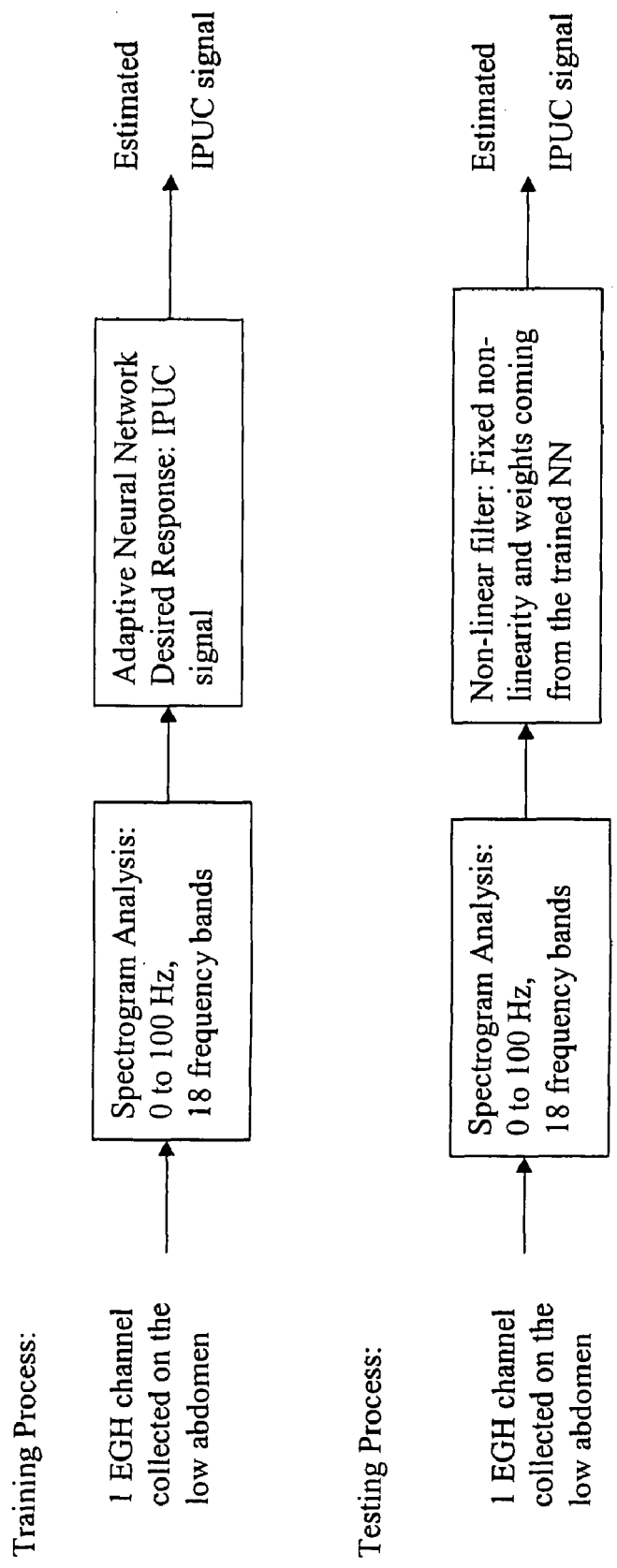
FIG. 13 illustrates the steps of training and testing processes for an intra-uterine pressure sensor of the invention.

In a preferred embodiment, the MLP has 18 input processing elements (PEs), 5 hidden layer PEs, and an output PE. Both the hidden and output layers have hyperbolic tangent non-linearities. As understood by skilled engineers in the field, the training stage on a neural network system is performed on a large number of data sets using an IUP catheter (IUPC), see FIG. 13. The data is passed through the network repeatedly, and each time an error between the desired output of the network and the actual output of the network is computed. This error is used to adjust the parameters of the network to reduce the error. After repeated training passes, the error is minimized and the neural network is ready for use (typically, at this point, the system parameters are fixed). In the testing process, a set of data that was not used for training is passed through the system to ensure that the neural network has appropriately learned the task.

As understood by the skilled clinician, IUP is not homogenous in the uterus. Current usage of IUP catheters provides imprecise IUP measurement because IUP catheter output depends on the position of the catheter, the volume of amniotic fluid, and the position of the patient. Because the sensors of the subject invention can be placed at various locations on the abdomen, the pressure calculated by different sensors gives a different value for each sensor. In a preferred embodiment, a sensor is placed low on the abdomen, near the lower part of the uterus.

EXAMPLE 1

Method for Personalizing a Sensor Mesh of the Invention

In one embodiment of the invention, a mesh of 20 electrodes was used to collect ECG signals. Each of the electrodes was selectively multiplexed into/out of the ICA and Pan Tompkins algorithm operations, depending on the quality of the signal and the TF for the fetal ECG output from Pan Tompkins operator(s). At the output of the ICA algorithm operator(s), the fetal ECG signal was correlated with 8 pre-filtered raw signals. The 8 correlation coefficients correspond to the influence of the fetal heart in the different electrodes. The electrodes with the lowest correlation coefficients were switched out of the ICA/Pan Tompkins algorithm operations and other electrodes were switched into those operations to find the best set of electrodes for finding the fetal ECG.

By providing a method for personalizing a sensor mesh, the subject invention combines cumbersome individual sensor leads into a single cable, to enable the system to easily determine optimal locations on the mother for sensor placement, to obtain optimal raw sensor signals (i.e., prior to filtration), and to improve patient comfort.

EXAMPLE 2

Maternal-Fetal Monitoring System of the Invention

Figure 14:
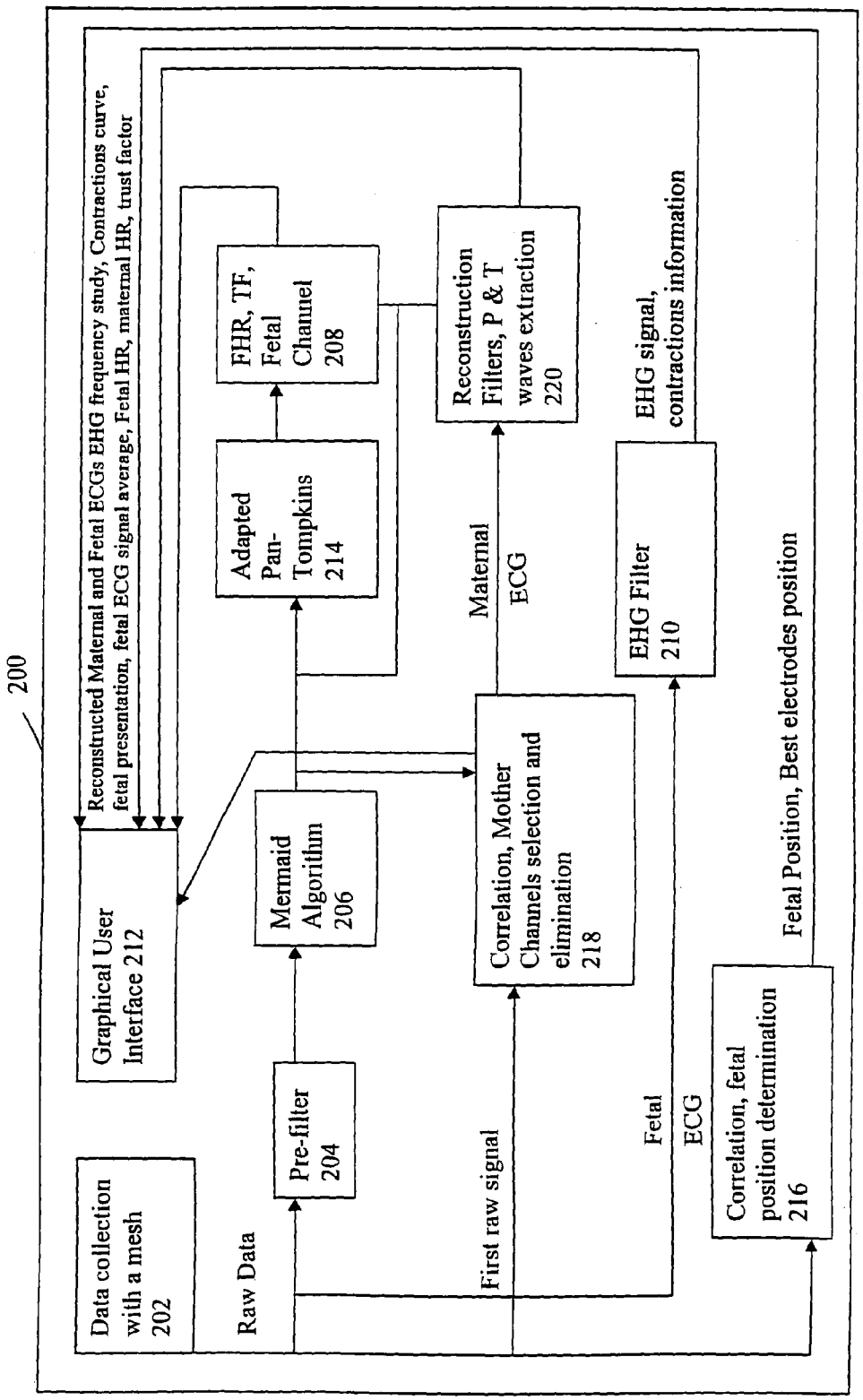
FIG. 14 is a flow diagram illustrating a maternal-fetal monitoring system of the invention.

As illustrated in FIG. 14, a maternal-fetal monitoring system 200 of the present invention is provided, wherein the system comprises an electrode mesh 202, an amplifier, at least one filter 204, and a processor for running an ICA algorithm 206, preferably Mermaid, and calculating a Trust Factor 208, to provide clinical information regarding maternal-fetal health. The electrode mesh has 10 electrodes, which are placed on the maternal abdomen. Electrodes having offset tabs that aid in eliminating noise artifacts are preferred. In this example, 1"¼ Blue sensor Ag/AgCl electrodes are used. A 10 lead shielded cable is used to connect the electrodes to the amplifier.

The amplifier of the subject invention takes into account the fetal ECG, which typically is around 10 µV to 50 µV in amplitude. In a preferred embodiment, the amplifier of the invention is a high-resolution, low-noise unipolar amplifier in which all channels are referenced from a single electrode. With this amplifier, a driven right leg (DRL) circuit is utilized to actively suppress noise and improve the common mode rejection ratio (CMRR) of the amplifier. The following is a nonlimiting list of preferred amplifier specifications of the subject invention: (1) number of channels=8; (2) gain is adjusted between 4,000 V/V and 10,000 V/V, but for practical purposes the gain is set to 4,500 V/V; (3) a pass band of 0.16 Hz and 100 Hz, with a 60 Hz notch filter; and (4) a CMRR of 80 dB.

The amplifier of this example has a 15-pin D-sub connector that interfaces with the 10-lead shielded ECG cable described above. The shielded cable aids in reducing any noise interference resultant from the 60 Hz transmitted from various power sources.

In accordance with the subject invention, the amplifier output interfaces to an analog to digital converter, for example a 16-bit PCMCIA A/D card. The A/D converter sends the data to a processor that enables recordation and storage of raw ECG signals prior to processing. The collected raw signals are a mixture of several sources that are theoretically independent: the maternal ECG, the fetal ECG, EMG signals and other noise sources. Onboard the amplifier system is an isolated power converter that protects the patient from high leakage currents.

At specific time intervals, preferably every 4 seconds, the channels corresponding to V1 and V2, V3 and V4 are combined by the processor and passed through a series of band pass filters 204, 210 to obtain an EHG spectrogram study and a contraction curve. These curves are plotted on a graphical user interface (GUI) 212 for the 2 leads V1-V2 and V3-V4. The contraction curve is plotted below the FHR, MHR trace. The spectral characteristics of the EHG curves can be utilized by the processor to predict contraction efficiency and preterm labor.

Also at specific time intervals, preferably every 4 seconds, raw signals from 8 channels are presented to a band pass filter 204. On the first 3 channels corresponding to LA, RA and V1 the maternal HR is computed on the 4 second segment of the data. The median of these 3 values is kept as the maternal HR.

A modified ICA algorithm 206 of the processor, preferably the MERMAID ICA algorithm, is then applied to the filtered signals from the electrodes. The output of the ICA algorithm is the estimated independent components, i.e. the estimated fetal ECG, maternal ECG, and other components. Generally, 2 to 3 signals are found as different projections of the maternal ECG, 1 or 2 signals are projections of the fetal ECG, and the other signals are noise, EHG, or other signals not of interest.

At those specific time intervals, preferably every 4 seconds, at the output of the ICA algorithm, in this instance the Mermaid ICA algorithm, several autocorrelation functions are computed on each output signal and a peak detection algorithm is computed to find the HR on this segment of data. On the same 8 signals, an adapted version of a Pan Tompkins QRS detection algorithm 214 is performed by the processor. The processor computes for each signal the probability Pm that the signal is a maternal signal. The signals that provide a Pm higher than 0.7 are stored by the processor as maternal signals. Then the probability Pf that the signal is a fetal signal is computed. The signal with the highest Pf is classified as the best fetal channel.

In accordance with the present invention, the processor derives the trust factor (TF) 208 by truncating the value of 10 times the highest remaining probability Pf. The TF 208 ranges from 0 to 10, with 10 corresponding to a probability of 1 that the detected fetal signal is actually the fetal ECG. 0 is the worst case where the heart rate that is found is certainly not the fetal heart rate. The trust factor also describes the quality of the fetal ECG signal since low variance and few FN and FP are characteristic of a clean ECG signal and are represented by a high TF. The processor saves and plots the FHR, MHR every 4 seconds on the graphical user interface (GUI). The trust factor can be displayed on the GUI 212 as well.

In a preferred embodiment, the GUI 212 includes an interface where the user positions the electrode on a drawing of a pregnant woman as they were placed on the patient. The electrode position is saved. Every electrode position change corresponds to a model of the fetal heart vector projection on the different leads for different fetal presentations: normal vertex, breech or lateral presentation. Templates of simulated fetal ECG waveforms corresponding to different fetal presentation in the uterus are thus provided. Every minute, each template is correlated 218 with the raw data at the location of the fetal QRS complex (found by the Pan Tompkins algorithm operations) and displays the fetal presentation that gives the highest correlation coefficient. In most cases, the fetal presentation is the vertex position (96%).

At the output of the ICA separation algorithm, the estimated fetal ECG signal is correlated 218 with the 8 channels of prefiltered raw signals. These 8 correlation coefficients correspond to the influence of the fetal heart electrical influence in the different electrodes. They are shown on the GUI 212 interface as a fetal electrical influence mapping.

The selected fetal ECG is passed through reconstruction filters 220 to reconstruct the shape of the waveforms that have been distorted by all the previous filters applied. The reconstructed FECG is plotted on the GUI 218 below the maternal ECG. An averaged FECG is calculated and plotted on the GUI 212. The different waveform intervals are computed and shown on the GUI 212.

This entire system (with a minimal user interface) can easily be constructed in a small, compact monitor that can be worn on a belt, similar to an ECG Holter monitor (approximately the size of a cigarette pack). It could also be built into an existing hospital monitor to provide additional information or replace the existing ultrasound/tocodynamometer system. Thus the system can be used as a home monitoring system (compact size and telecommunications ability) or a hospital monitoring system.

EXAMPLE 3

Comparison of Intra-Uterine Pressure Values Using a Neural Network of the Subject Invention versus an Intra-Uterine Pressure Catheter (IUPC)

Figure 15A:
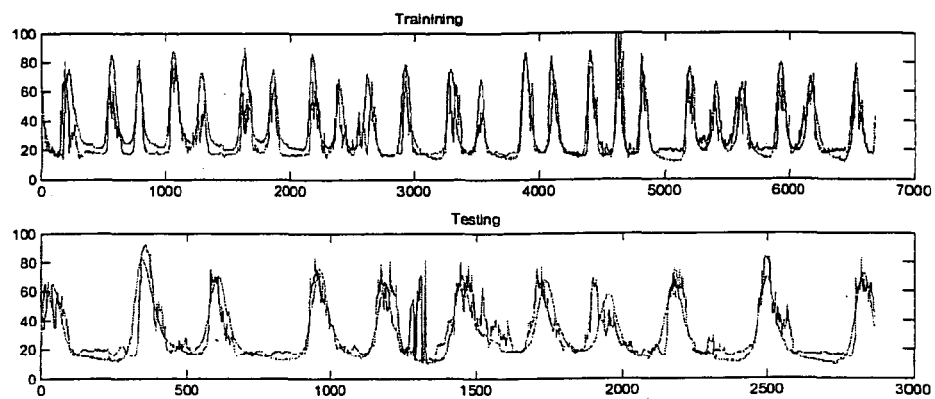
FIGS. 15A-C graphically illustrate intra-uterine pressure signals from collected versus training sensor signals for signals collected by abdominal sensors of the subject invention as compared to signals provided by a commercially available intra-uterine pressure catheter.
Figure 15B:
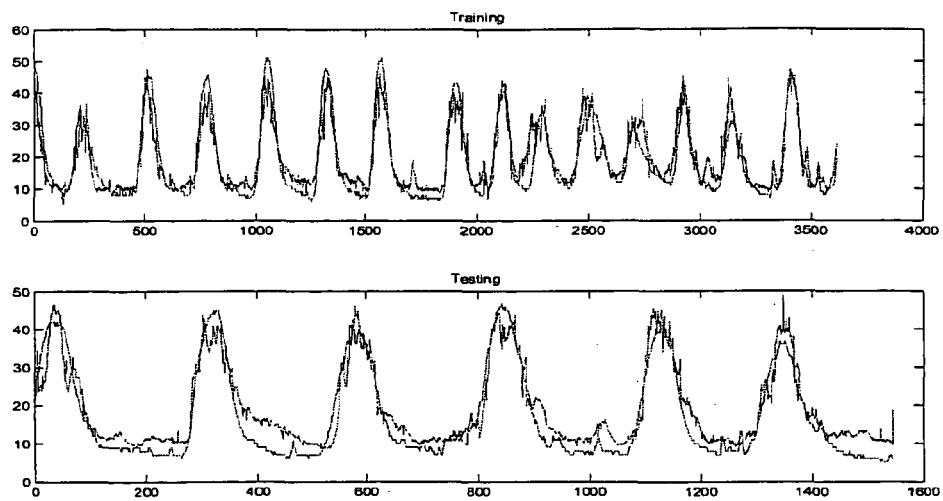
Figure 15C:
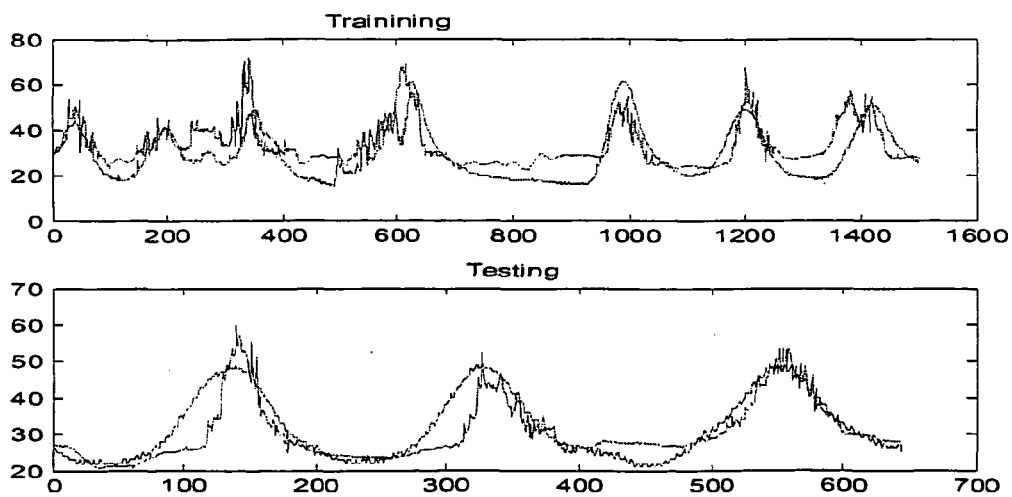

An intelligence system (i.e., neural network system) has been trained to predict the IUP from the electrical signals obtained from the abdominal ECG electrodes (EHG). The network was trained with three different patients and can be used to create an estimated non-invasive measure of IUP in patients. FIGS. 15A-C show the output of the neural network and the IUPC signal for three different data sets A, B, and C. The mean squared error (MSE) and correlation coefficient (CorrCoef) for each data set are provided in Table 1. As can be seen most of the peaks in a commercially available IUP catheter signal are well captured by the neural network of the subject invention. The high correlation coefficient in test data further supports the fact that the network has learnt the relationship.

TABLE 1

Quantitative Comparison of Values from an MLP of the Invention

|  | Training | | Testing | |
| --- | --- | --- | --- | --- |
| Data Set | MSE | CorrCoef | MSE | CorrCoef |
| A | 165.131266 | 0.804183 | 132.039448 | 0.810358 |
| B | 24.256377 | 0.914247 | 20.674292 | 0.941033 |
| C | 79.525224 | 0.704184 | 25.695268 | 0.842167 |

EXAMPLE 4

Comparison of Contraction Characteristics Analyzed in Accordance with the Monitoring System of the Subject Invention versus Commercially Available Contraction Monitor The EHG extraction operation of the subject invention was applied to 6 different data sets, wherein each set was analyzed for their contraction characteristics and the results provided to the user. The observations for data set D is presented in detail in Tables 2 and 3, wherein observations from a commercially available EHG monitor (Corometrics) is provided in Table 2 and observations using the EHG extraction operations of the invention are provided in Table 3.

Figure 16:
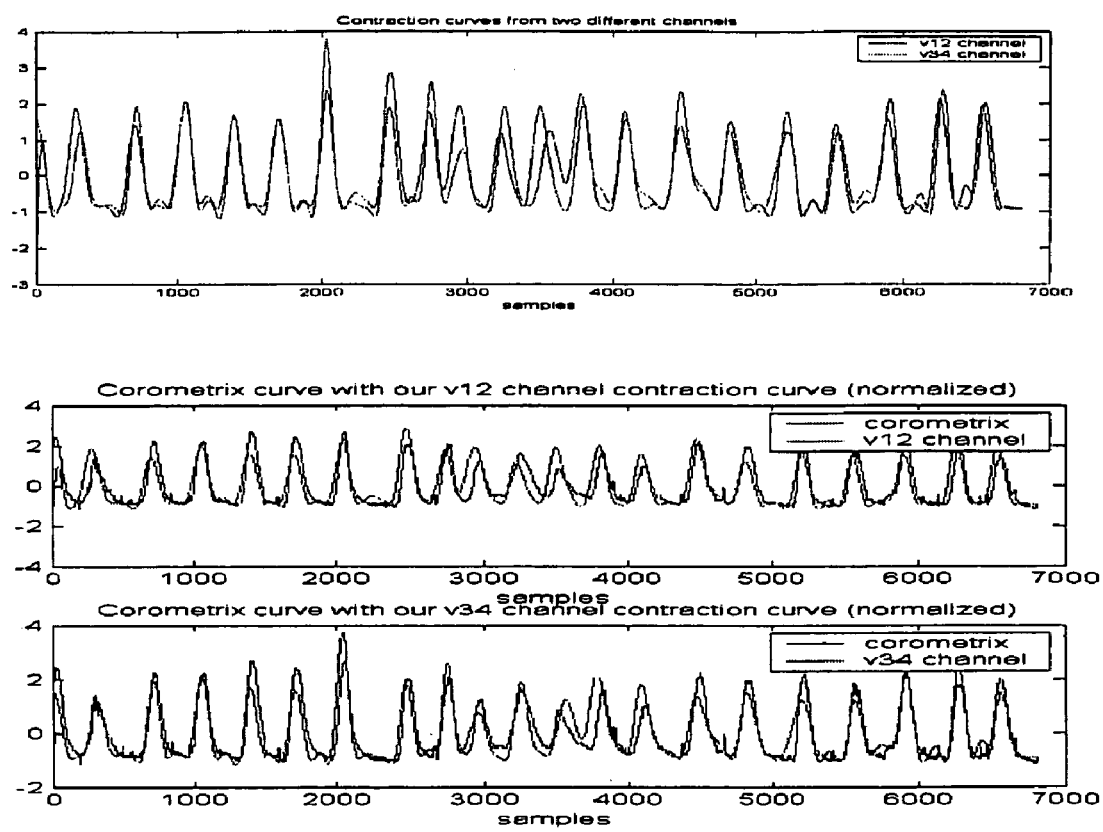
FIG. 16 are graphical illustrations of contraction curves of sensors channels $1_{V1-V2}$ and $1_{V3-V4}$ of the subject invention in comparison to contraction curves provided by a commercially available Corometrics monitoring system.

FIG. 16 gives the contraction curves of both channels $1_{V1-V2}$ (EHG I) and $1_{V3-V4}$ (EHG II) (illustrations of electrode location provided in FIGS. 9A and 9B) along with the corometrics contraction curve. Note that here both contraction curves are normalized in order to take into account the disparity in amplitude of the signals. A further quantitative comparison between the normalized EHG and Corometrics is achieved by computing their mean squared error and correlation coefficient, see Tables 2 and 3.

TABLE 2

EHG results using Corometrics

| N (CORO) | Start [h:min:sec] | Duration [h:min:sec] | Peak | Peak Location [h:min:sec] |
| --- | --- | --- | --- | --- |
| 1 | 00:00:00 | 00:00:41 | 48 | 00:00:08 |
| 2 | 00:01:44 | 00:00:42 | 36 | 00:01:55 |
| 3 | 00:04:06 | 00:00:51 | 46 | 00:04:26 |

TABLE 2-continued

EHG results using Corometrics

| N (CORO) | Start [h:min:sec] | Duration [h:min:sec] | Peak | Peak Location [h:min:sec] |
|---|---|---|---|---|
| 4 | 00:06:14 | 00:00:52 | 46 | 00:06:40 |
| 5 | 00:08:33 | 00:00:49 | 51 | 00:08:49 |
| 6 | 00:10:50 | 00:00:51 | 48 | 00:11:07 |
| 7 | 00:12:52 | 00:00:53 | 51 | 00:13:15 |
| 8 | 00:15:42 | 00:00:42 | 43 | 00:15:57 |
| 9 | 00:17:27 | 00:00:41 | 44 | 00:17:46 |
| 10 | 00:18:58 | 00:00:34 | 34 | 00:19:12 |
| 11 | 00:20:34 | 00:01:01 | 40 | 00:20:56 |
| 12 | 00:24:13 | 00:00:38 | 39 | 00:24:35 |
| 13 | 00:26:00 | 00:00:48 | 32 | 00:26:18 |
| 14 | 00:28:12 | 00:00:47 | 46 | 00:28:37 |
| 15 | 00:30:11 | 00:00:54 | 43 | 00:30:35 |
| 16 | 00:32:38 | 00:00:43 | 45 | 00:32:54 |
| 17 | 00:34:46 | 00:00:49 | 41 | 00:35:05 |
| 18 | 00:36:57 | 00:00:51 | 47 | 00:37:19 |
| 19 | 00:39:20 | 00:00:42 | 40 | 00:39:36 |
| 20 | 00:41:11 | 00:00:43 | 37 | 00:41:28 |

TABLE 3

EHG results using EHG extraction operations

| N (EHG-II) | Start [h:min:sec] | Duration [h:min:sec] | Peak | Peak Location [h:min:sec] |
|---|---|---|---|---|
| 1 | 00:00:01 | 00:00:32 | 2074.2 | 00:00:00 |
| 2 | 00:01:39 | 00:00:40 | 1994.1 | 00:01:59 |
| 3 | 00:04:05 | 00:00:42 | 2553.4 | 00:04:25 |
| 4 | 00:06:10 | 00:00:50 | 2573.1 | 00:06:33 |
| 5 | 00:08:29 | 00:00:38 | 2369.2 | 00:08:47 |
| 6 | 00:10:50 | 00:00:35 | 2188.3 | 00:11:07 |
| 7 | 00:12:50 | 00:00:43 | 4093.7 | 00:13:09 |
| 8 | 00:15:36 | 00:00:41 | 2408.1 | 00:15:55 |
| 9 | 00:17:27 | 00:00:40 | 3224.3 | 00:17:45 |
| 10 | 00:18:47 | 00:00:43 | 1584.2 | 00:19:11 |
| 11 | 00:20:36 | 00:00:46 | 2472.4 | 00:20:57 |
| 12 | 00:22:29 | 00:00:57 | 1853.9 | 00:22:54 |
| 13 | 00:23:48 | 00:01:00 | 2761.5 | 00:24:17 |
| 14 | 00:25:47 | 00:01:00 | 2369.7 | 00:26:10 |
| 15 | 00:28:04 | 00:01:11 | 2054.3 | 00:28:25 |
| 16 | 00:30:10 | 00:01:01 | 2167.1 | 00:30:31 |
| 17 | 00:32:13 | 00:01:07 | 1837.7 | 00:32:58 |
| 18 | 00:34:47 | 00:00:41 | 1885.9 | 00:35:05 |
| 19 | 00:36:56 | 00:00:46 | 2713.1 | 00:37:21 |
| 20 | 00:39:20 | 00:00:39 | 2953.8 | 00:39:40 |
| 21 | 00:41:11 | 00:00:43 | 2649.9 | 00:41:30 |

Figure 17:
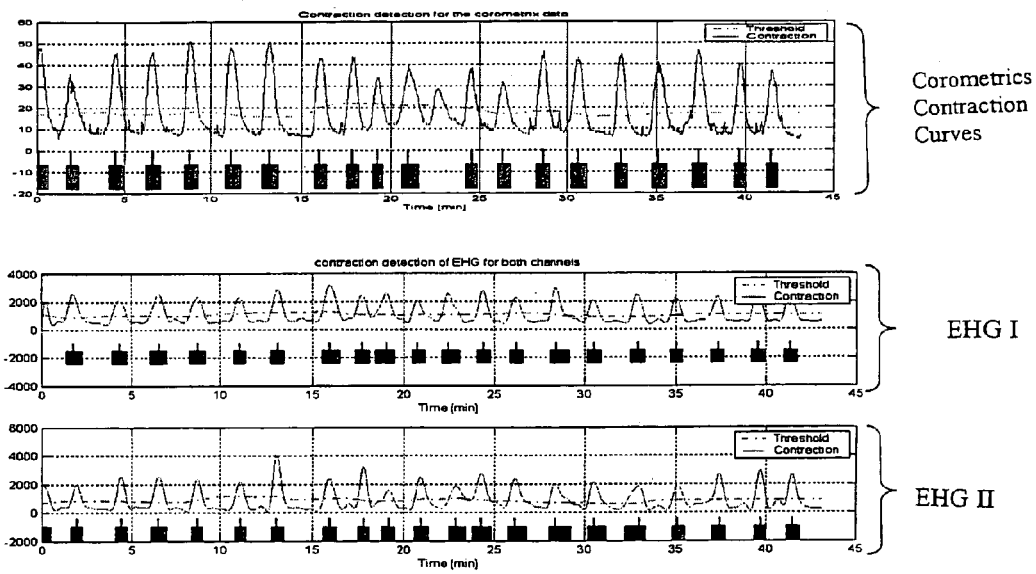
FIG. 17 are graphical illustrations of contractions detected using the monitoring system of the subject invention as compared to a commercially available Corometrix monitoring system.

FIG. 17 shows each contraction waveform along with their computed threshold. This figure also shows the detected contractions with small rectangles each having width corresponding to the particular contraction duration. Note that peak location is also marked in FIG. 17. The starting time, duration, maximum amplitude and location of maximum for each contraction are estimated and are tabulated below. As can be seen from the table the starting time of each detected contraction in most cases precedes that of the Corometrics. This is entirely logical since the electrical excitation should precede the muscle contraction.

Figure 18:
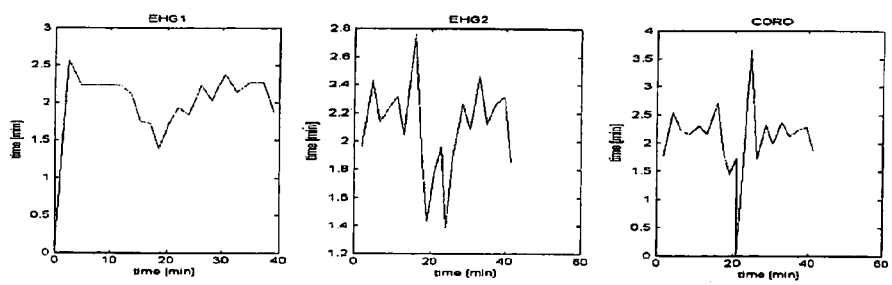
FIG. 18 are graphical illustrations comparing observed time intervals between successive contractions as time progresses using a monitoring system of the invention (EHG2) versus a commercially available Corometrix monitoring system.
Figure 19A:
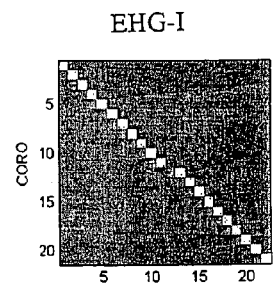
FIGS. 19A-D are graphical illustrations of contraction consistency between a monitoring system of the subject invention and a commercially available Corometrics monitoring system.
Figure 19B:
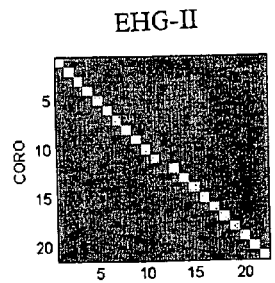
Figure 19C:
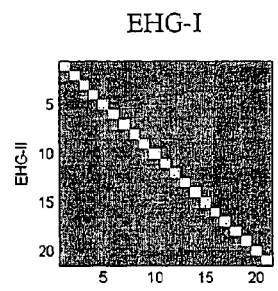
Figure 19D:
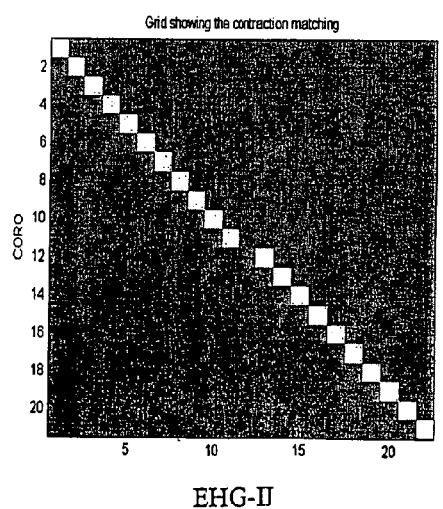

FIG. 18 shows the time interval between successive contractions as observed by the monitoring system of the invention as compared to a Corometics monitoring system. Such data can be significant since the onset of delivery is marked by rigorous uterine activity with a decreasing time span between consecutive contractions. A further and final comparison of EHG contraction waveform with a commercially available Corometrics counterpart is carried out for their contraction consistency. The result is presented graphically on a grid, as illustrated in FIGS. 19A-D. Row and column numbers denote the consecutive contraction numbers detected by both Corometrics and EHG (FIGS. 19A-19B). Note that there are two channels of EHG data. An additional grid of the first channel of EHG versus the second channel is also given in FIG. 19C. Perfect agreement between measured and predicted contractions corresponds to a diagonal pattern of values on the grid FIG. 19D.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A maternal-fetal monitoring system comprising:
   a) at least two surface sensors to receive a mixture of maternal and fetal vital signals, wherein the mixture of maternal and fetal vital signals comprises at least one EHG signal; and
   b) a computing means for analyzing the mixture of maternal and fetal vital signals from the sensors, said computing means including hardware and software, wherein said software comprises a means for converting the at least one EHG signal directly into montevideo units without first calculating an intrauterine pressure curve.

2. The maternal-fetal monitoring system of claim 1, wherein said computing means comprises a neural network system.

3. The maternal-fetal monitoring system of claim 1, wherein the at least one EHG signal has a frequency in a range of 0.16 Hz to 100 Hz.

4. A maternal-fetal monitoring system comprising:
   a) at least two surface sensors to receive a mixture of maternal and fetal vital signals; and
   b) a computing means for analyzing the mixture of maternal and fetal vital signals from the sensors, said computing means including hardware and software, wherein said software comprises a means for extracting EHG to provide at least one EHG spectrogram having at least one characteristic;
   wherein said characteristic is associated with a feature selected from the group consisting of contraction efficiency, probability of vaginal delivery, time to delivery, arrested descent, the effectiveness of drugs used to induce labor, uterine rupture, and post-delivery maternal uterine tone.

5. The maternal-fetal monitoring system of claim 4, wherein said software means further comprises an analyzing means for identifying in the EHG spectrogram said special characteristic and for providing said analysis with regard to said feature to the user.

6. The maternal-fetal monitoring system of claim 4, further comprising a sensor to receive abdominal muscle signals; wherein said software means further comprises a biofeedback means for directing maternal pushing efforts during labor.

7. The maternal-fetal monitoring system of claim 4, wherein said characteristic is associated with a feature selected from the group consisting of contraction efficiency and the effectiveness of drugs used to induce labor.

8. The maternal-fetal monitoring system of claim 7, wherein said characteristic is associated with contraction efficiency.

9. The maternal-fetal monitoring system of claim 7, wherein said characteristic is associated with the effectiveness of drugs used to induce labor.

10. The maternal-fetal monitoring system of claim 4, wherein said characteristic is associated with probability of vaginal delivery.

11. The maternal-fetal monitoring system of claim 4, wherein said characteristic is associated with time to delivery.

12. The maternal-fetal monitoring system of claim 4, wherein said characteristic is associated with arrested descent.

13. The maternal-fetal monitoring system of claim 4, wherein said characteristic is associated with uterine rupture.

14. The maternal-fetal monitoring system of claim 4, wherein said characteristic is associated with post-delivery maternal uterine tone.

15. The maternal-fetal monitoring system of claim 4, wherein the EHG spectrogram directly and reliably predicts the feature.

16. The maternal-fetal monitoring system of claim 4, wherein the EHG signal extracted to provide the at least one EHG spectrogram has a frequency in a range of 0.16 Hz to 100 Hz.

17. The maternal-fetal monitoring system of claim 7, wherein the EHG signal extracted to provide the at least one EHG spectrogram has a frequency in a range of 0.16 Hz to 100 Hz.

* * * * *